(12) United States Patent
Fukushi et al.

(10) Patent No.: US 10,252,006 B2
(45) Date of Patent: Apr. 9, 2019

(54) SYRINGE ASSEMBLY, SYRINGE ASSEMBLY PACKAGING, OUTER CYLINDER SEAL CAP, AND PREFILLED SYRINGE

(71) Applicant: TERUMO KABUSHIKI KAISHA, Tokyo (JP)

(72) Inventors: Keiko Fukushi, Hadano (JP); Yoshihiko Abe, Odawara (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 208 days.

(21) Appl. No.: 15/455,835

(22) Filed: Mar. 10, 2017

(65) Prior Publication Data

US 2017/0182259 A1 Jun. 29, 2017

Related U.S. Application Data

(63) Continuation of application No. PCT/JP2015/073416, filed on Aug. 20, 2015.

(30) Foreign Application Priority Data

Sep. 11, 2014 (JP) .................................. 2014-185429

(51) Int. Cl.
*A61M 5/28* (2006.01)
*A61M 5/32* (2006.01)
(Continued)

(52) U.S. Cl.
CPC ........... *A61M 5/3202* (2013.01); *A61L 31/00* (2013.01); *A61L 31/048* (2013.01); *A61L 31/10* (2013.01);
(Continued)

(58) Field of Classification Search
CPC ...... A61M 5/3202; A61M 5/002; A61M 5/32; A61M 5/28; B65D 25/108;
(Continued)

(56) References Cited

U.S. PATENT DOCUMENTS

| 5,000,994 A | 3/1991 | Romberg et al. |
| 5,354,286 A | 10/1994 | Mesa et al. |

(Continued)

FOREIGN PATENT DOCUMENTS

| JP | S61-106172 A | 5/1986 |
| JP | 2006-314554 A | 11/2006 |

(Continued)

OTHER PUBLICATIONS

International Search Report dated Dec. 1, 2015 in PCT/JP2015/073416.
Written Opinion of the International Searching Authority dated Dec. 1, 2015 in PCT/JP2015/073416.
(Continued)

*Primary Examiner* — Anthony D Stashick
*Assistant Examiner* — James M Van Buskirk
(74) *Attorney, Agent, or Firm* — Foley & Lardner LLP

(57) ABSTRACT

A syringe assembly of the present invention is composed of an outer cylinder and a seal cap. The outer cylinder has an outer cylinder body part, a piercing needle mounting part, and a piercing needle fixed to the piercing needle mounting part. The seal cap has a closed distal end part, an open proximal end part, a piercing needle mounting part-accommodating part accommodating a distal end portion of the piercing needle mounting part, a piercing needle accommodating part, and a pierceable part into which the piercing needle tip is pierceable. A polyparaxylylene coating is provided on an inner surface of the piercing needle mounting part-accommodating part of the seal cap or on an outer surface of the piercing needle mounting part of the outer cylinder. The inner surface of the piercing needle mounting part-accommodating part of the seal cap and the outer surface of the piercing needle mounting part of the outer cylinder are kept in close contact with each other through the polyparaxylylene coating.

10 Claims, 13 Drawing Sheets

(51) Int. Cl.
*A61L 31/00* (2006.01)
*A61L 31/10* (2006.01)
*B65D 77/20* (2006.01)
*A61M 5/00* (2006.01)
*A61L 31/04* (2006.01)
*B65D 25/10* (2006.01)
*B65D 43/02* (2006.01)

(52) U.S. Cl.
CPC .............. *A61M 5/002* (2013.01); *A61M 5/28* (2013.01); *A61M 5/32* (2013.01); *B65D 25/108* (2013.01); *B65D 43/0202* (2013.01); *B65D 77/20* (2013.01); *B65D 2543/00537* (2013.01)

(58) Field of Classification Search
CPC ................ B65D 43/0202; B65D 77/20; B65D 2543/00537; A61L 31/10; A61L 31/048; A61L 31/00
USPC ......................................................... 206/366
See application file for complete search history.

(56) References Cited

U.S. PATENT DOCUMENTS

| | | | |
|---|---|---|---|
| 6,719,732 | B2 | 4/2004 | Courteix |
| 8,939,941 | B2 | 1/2015 | Thibault et al. |
| 2010/0145150 | A1 | 6/2010 | Fukunaga |
| 2013/0012886 | A1 | 1/2013 | Kawachi |
| 2014/0353190 | A1 | 12/2014 | Okihara et al. |
| 2015/0190566 | A1 | 7/2015 | Okihara |
| 2017/0189603 | A1 | 7/2017 | Okihara et al. |

FOREIGN PATENT DOCUMENTS

| | | |
|---|---|---|
| JP | 2010-131153 A | 6/2010 |
| JP | 2010-534546 A | 11/2010 |
| WO | WO 2011/114917 A1 | 9/2011 |
| WO | WO-2013/125443 A1 | 8/2013 |
| WO | WO-2014/102987 A | 7/2014 |

OTHER PUBLICATIONS

International Preliminary report on Patentability dated Mar. 14, 2017 in PCT/JP2015/073416.
Extended European Search Report dated Mar. 27, 2018 in corresponding application No. 15840367.5.

SYRINGE ASSEMBLY, SYRINGE ASSEMBLY PACKAGING, OUTER CYLINDER SEAL CAP, AND PREFILLED SYRINGE

CROSS-REFERENCE TO RELATED APPLICATIONS

This application is a continuation of PCT Application No. PCT/JP2015/073416, filed on Aug. 20, 2015, which claims priority to Japanese Patent Application No. 2014-185429, filed on Sep. 11, 2014, the entireties of which are hereby incorporated by reference.

TECHNICAL FIELD

The present invention relates to a seal cap for an outer cylinder, a syringe assembly having the seal cap mounted on the outer cylinder, and a prefilled syringe using the syringe assembly having the seal cap mounted on the outer cylinder, and a packaging body accommodating a plurality of syringes assemblies.

BACKGROUND ART

As an insulin syringe and the like for administering a small amount of a medical agent to a patient, a syringe having a piercing needle fixed to the distal end of an outer cylinder is used. In constructing a prefilled syringe in which a medical agent is filled in advance by using a syringe of this type, it is necessary to seal the tip of the needle. A cap capable of sealing the tip of the needle is proposed, as disclosed in Japanese translation of PCT International Application Publication No. 2010-534546 (patent document 1) and U.S. Pat. No. 6,719,732 (patent document 2).

PRIOR ART DOCUMENTS

Patent Documents

Patent document 1: Japanese translation of PCT International Application Publication No. 2010-534546
Patent document 2: U.S. Pat. No. 6,719,732

SUMMARY OF THE INVENTION

Problems to be Solved by the Invention

The seal cap (shield 10) of the patent document 1 covers the tip of the syringe (a part of the syringe is shown in FIG. 2 of patent document 1). The tip of the syringe 3 has the hub 2 to which the needle 6 is fixed. The shield 10 has the open proximal end 11, the closed tip 12, and the wall 13 extended from the proximal end 11 to the closed tip 12. The inner surface 14 of the wall 13 defines the cavity 15 accommodating a part of the tip of the syringe 3. For example, in a case where the shield 10 is fixed to the tip of the syringe to protect the tip while a syringe is being transported, the portion 14a of the inner surface 14 contacts the hub 2 disposed at the tip of the syringe 3.

In the shield of the patent document 1 shown in FIG. 3, the portion 14a of the inner surface 14 of the wall 13 has a plurality of grooves 16. The grooves 16 are arranged regularly along the periphery of the portion 14a and parallel with the longitudinal axis A of the shield 10. The grooves 16 allow air to flow while an operation of mounting the shield on the hub 2 is being performed. The area of the adhesive surface of the shield becomes small, which allows the shield to be easily mounted on the hub and the longitudinal axis A of the shield 10 and the longitudinal axis B (see FIG. 2) of the injection device 3 to easily maintain confounding. Therefore, the shield 10 of the invention is fixed to the distal end of the injection device 3 completely and accurately. The grooves having the peculiar roughness of the portion 14a of the inner surface 14 of the wall 13 allows the shield 10 to be easily removed from the distal end of the injection device 3 when the injection device 3 is used.

In the seal cap (device for protecting the syringe needle) of the patent document 2 (U.S. Pat. No. 6,719,732), as shown in FIGS. 1 through 5 of the patent document 2, the elastic needle cap 20 extended longitudinally between the open proximal end 22 and the closed tip 24 has the inner housing 26 partitioned by the lateral direction wall 28 and the end wall 30. Between the first and second portions 40 and the portion 42 of the housing 26, the annular bead (rib) 70 expanded inward is formed at the edge of the second portion 42 extended toward the proximal end 22. To improve the deformability of the annular bead 70 and facilitate the passing of the pressurized water vapor through the annular bead 70, four slots 72 longitudinally extended are formed on the bead 70.

In the seal cap of the patent document 1, the inner surface of the seal cap (shield 10) and the outer surface of the distal end portion of the outer cylinder are kept in direct contact. Thus in a case where the shield 10 is stored with the shield being mounted on the outer cylinder, there is a fear that the shield 10 sticks to the outer cylinder. Further when the shield 10 and the outer cylinder undergoes high-pressure steam sterilization or ethylene oxide gas sterilization which subjects the shield 10 and the outer cylinder to the receipt of the application of a pressure load, the shield 10 is pressed against the outer cylinder. As a result, there is a large area of direct contact between the inner surface of the shield 10 and the outer surface of the distal end portion of the outer cylinder. Thus there is a fear that the shield 10 sticks to the outer cylinder to a higher extent.

In the seal cap of the patent document 2, the annular bead (rib) 70 is formed on the inner surface of the seal cap (elastic needle cap 20) by inwardly expanding the annular bead. The four slots 72 are formed on the bead 70 by extending it longitudinally. There is a large area of direct contact between the inner surface of the elastic needle cap 20 and the outer surface of the distal end portion of the outer cylinder. Thus, there is a fear that the elastic needle cap 20 sticks to the outer cylinder in a case where elastic needle cap 20 is stored with the elastic needle cap being mounted on the outer cylinder. Further when the elastic needle cap 20 and the outer cylinder undergo high-pressure steam sterilization or ethylene oxide gas sterilization which subjects the elastic needle cap 20 and the outer cylinder to the receipt of the application of a pressure load, the elastic needle cap 20 is pressed against the outer cylinder. As a result, there is a large area of close contact between the inner surface of the elastic needle cap 20 and the outer surface of the distal end portion of the outer cylinder. Thus there is a fear that the elastic needle cap 20 sticks to the outer cylinder to a higher extent.

Therefore, it is an object of the present invention to provide a seal cap for an outer cylinder capable of preventing an inner surface of the seal cap and an outer surface of a distal end portion of the outer cylinder from sticking to each other and preventing the seal cap from being removed from the outer cylinder in a case where a syringe assembly having the seal cap mounted on the outer cylinder is stored with the seal cap being mounted on the outer cylinder and even in a case where as a method of sterilizing the syringe assembly, the syringe assembly undergoes high-pressure steam sterilization or ethylene oxide gas sterilization which subjects the syringe assembly to the receipt of the application of a pressure load, the syringe assembly having the seal cap mounted on the outer cylinder, a prefilled syringe using the syringe assembly having the seal cap mounted on the outer cylinder, and a packaging body accommodating a plurality of syringe assemblies.

Means for Solving the Problems

The above-described object can be achieved by a syringe assembly constructed as described below.

The present invention provides a syringe assembly comprising an outer cylinder having a cylindrical piercing needle mounting part, a piercing needle fixed the cylindrical piercing needle mounting part and a seal cap. The seal cap has a closed distal end part, an open proximal end part, a piercing needle mounting part-accommodating part accommodating a distal end portion of the piercing needle mounting part and a piercing needle accommodating part accommodating the piercing needle, and a pierceable part into which the piercing needle tip is pierceable. A polyparaxylylene coating is provided on an inner surface of the piercing needle mounting part-accommodating part of the seal cap or/and on an outer surface of the piercing needle mounting part of the outer cylinder. The seal cap is mounted on the outer cylinder. The inner surface of the piercing needle mounting part-accommodating part of the seal cap and the outer surface of the piercing needle mounting part of the outer cylinder are kept in close contact with each other through the polyparaxylylene coating.

The above-described object can be achieved by a prefilled syringe constructed as described below.

The present invention provides a prefilled syringe composed of the syringe assembly, a gasket which is accommodated inside the outer cylinder and liquid-tightly slidable inside the outer cylinder, and a medical agent filled inside a space formed of the outer cylinder and the gasket.

The above-described object can be achieved by a seal cap for an outer cylinder constructed as described below.

The present invention provides a seal cap, for an outer cylinder, mounting on the outer cylinder having an outer cylinder body part, a cylindrical piercing needle mounting part provided at a distal end portion of the outer cylinder body part and having an annular head portion and an annular concave portion formed at a proximal end of the annular head portion, and a piercing needle fixed to the piercing needle mounting part. The seal cap has a closed distal end part, an open proximal end part, a piercing needle mounting part-accommodating part accommodating a distal end portion of the piercing needle mounting part and a piercing needle accommodating part accommodating the piercing needle, a pierceable part into which a piercing needle tip of the piercing needle is pierceable, and a projected part formed on an inner surface of the piercing needle mounting part-accommodating part. A polyparaxylylene coating is formed on the inner surface of the piercing needle mounting part-accommodating part, when the seal cap is mounted on the outer cylinder, the piercing needle tip is pierced into the pierceable part of the seal cap; and when the projected part and the annular concave portion engage each other, the inner surface of the piercing needle mounting part-accommodating part and an outer surface of the piercing needle mounting part closely contact each other through the polyparaxylylene coating.

The above-described object can be achieved by a syringe assembly packaging body constructed as described below.

The present invention provides a syringe assembly packaging body, accommodating a plurality of the above syringe assemblies. The packaging body is composed of a container body whose upper surface is open and which has shape retainability, an outer cylinder holding member capable of holding a plurality of the syringe assemblies, a plurality of the syringe assemblies held by the outer cylinder holding member, a sheet-shaped lid member which airtightly seals the open upper surface of the container body and is peelable therefrom, and an air-permeable part, having bacteria impermeability and sterilizing gas permeability, which is provided on the container body or on the sheet-shaped lid member, and the packaging body has subjected to high-pressure steam sterilization or ethylene oxide gas sterilization.

MODE FOR CARRYING OUT THE INVENTION

Figure 1:
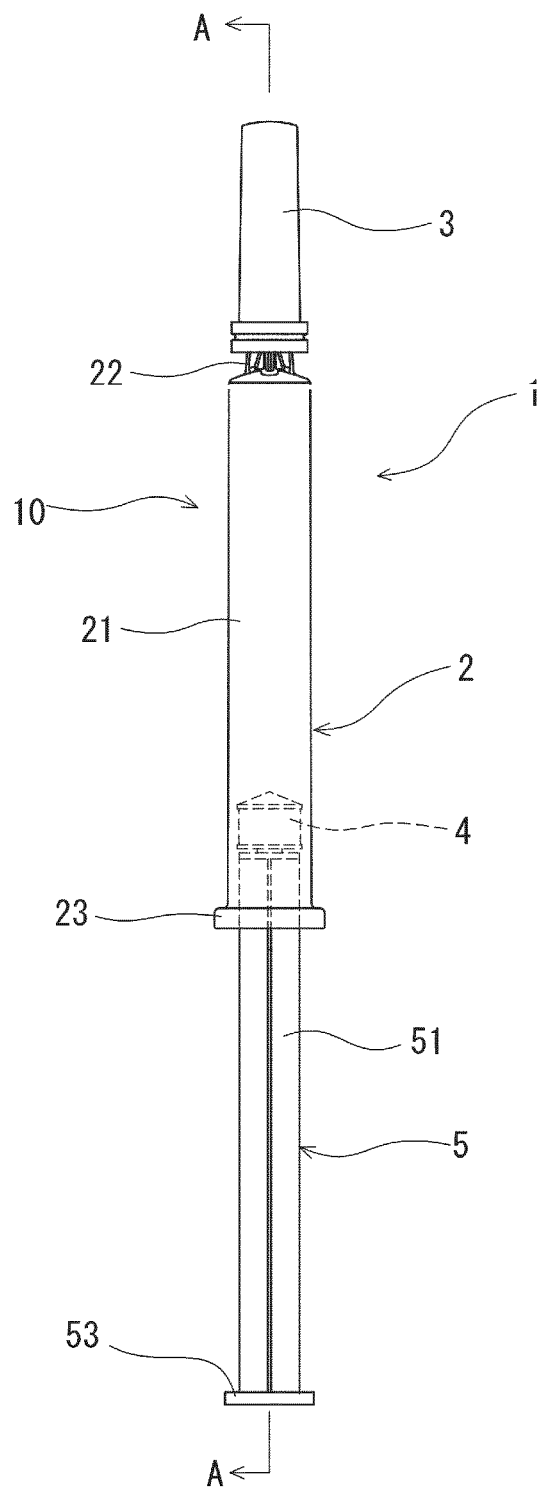
FIG. 1 is a front view of a prefilled syringe of an embodiment of the present invention.

A seal cap of the present invention for an outer cylinder, a syringe assembly of the present invention having the seal cap mounted on the outer cylinder, and a prefilled syringe of the present invention using the syringe assembly having the seal cap mounted on the outer cylinder are described below by using the embodiments shown in the drawings.

A prefilled syringe 1 of the present invention is composed of a syringe assembly 10, a gasket 4 which is accommodated inside the syringe assembly 10 and liquid-tightly slidable inside the syringe assembly 10, and a medical agent 8 filled inside a space formed of the syringe assembly 10 and the gasket 4.

The syringe assembly 10 (in other words, piercing needle-equipped outer cylinder on which cap is mounted, or outer cylinder assembly) of the present invention is composed of an outer cylinder 2 and a seal cap 3 mounted on the outer cylinder 2.

The outer cylinder 2 has an outer cylinder body part 21, a cylindrical piercing needle mounting part 22 provided at a distal end portion of the outer cylinder body part 21, and a piercing needle 6, having a piercing needle tip 61 at its distal end, whose proximal end portion is inserted into the piercing needle mounting part 22 and fixed thereto.

The seal cap 3 has a closed distal end part 31, an open proximal end part 32, a piercing needle mounting part-accommodating part 35 positioned at a side distal from the open proximal end part 32 and accommodating a distal end portion of the piercing needle mounting part 22, a hollow part 30 continuous with a distal end of the piercing needle mounting part-accommodating part 35 and having a piercing needle accommodating part 34 accommodating the piercing needle 6, and a pierceable part 33 into which the piercing needle tip 61 of the piercing needle 6 accommodated inside the piercing needle accommodating part 34 is pierceable.

A polyparaxylylene coating is provided on an inner surface of the piercing needle mounting part-accommodating part 35 of the seal cap 3. Instead of the inner surface of the piercing needle mounting part-accommodating part 35 of the seal cap 3, the polyparaxylylene coating may be provided on an outer surface of the piercing needle mounting part 22 of the outer cylinder 2. The polyparaxylylene coating may be provided on both the inner surface of the piercing needle mounting part-accommodating part 35 and the outer surface of the piercing needle mounting part 22 of the outer cylinder 2. In the syringe assembly 10, the seal cap 3 is mounted on the outer cylinder 2; the piercing needle tip 61 is pierced into the pierceable part 33 of the seal cap 3; and the inner surface of the piercing needle mounting part-accommodating part 35 of the seal cap 3 and the outer surface of the piercing needle mounting part 22 of the outer cylinder 2 are kept in close contact with each other through the polyparaxylylene coating.

Figure 2:
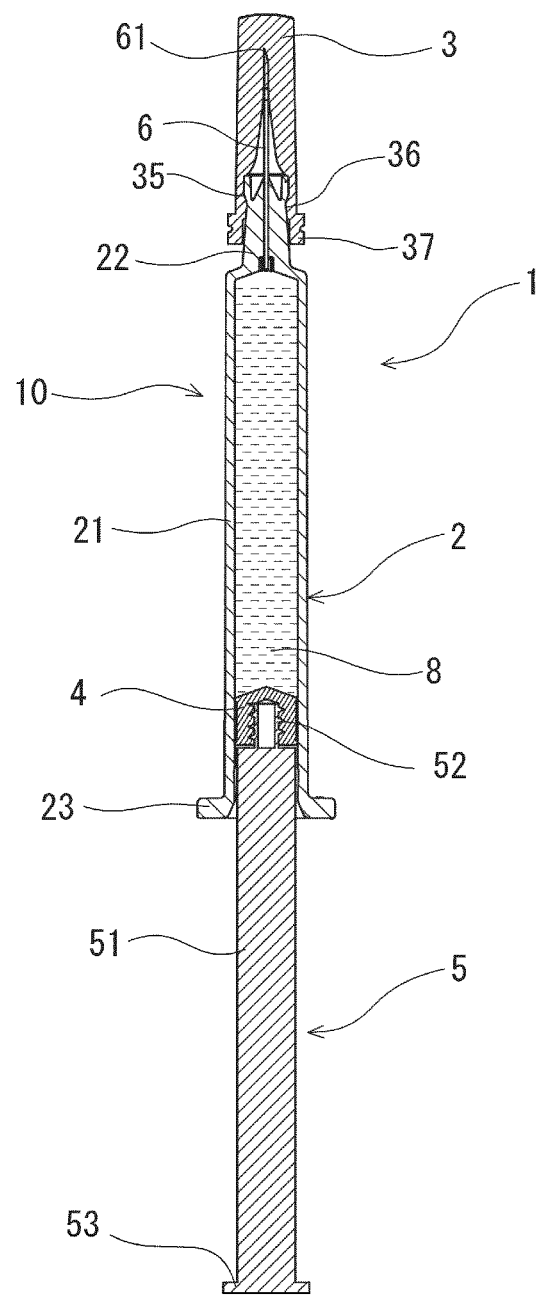
FIG. 2 is a sectional view taken along a line A-A of FIG. 1.

As shown in FIGS. 1 and 2, the prefilled syringe 1 is composed of the syringe assembly 10, which consists of the outer cylinder 2 and the seal cap 3 mounted on the outer cylinder 2 so as to seal the needle tip of the piercing needle, the gasket 4 which is accommodated inside the syringe assembly 10 and liquid-tightly slidable inside the syringe assembly 10, the medical agent 8 filled inside the space formed of the syringe assembly 10 and the gasket 4, and a plunger 5 mounted on the gasket 4 in advance or when the prefilled syringe is used.

The medical agent 8 is filled inside the space formed of the outer cylinder 2, the gasket 4, and the seal cap 3.

Any medical agent can be used as the medical agent 8 to be filled inside the above-described space. Examples of the medical agent 8 include high-concentration sodium chloride injection solution, minerals, heparin sodium aqueous solution, nitroglycerin, isosorbide dinitrate, cyclosporine, benzodiazepine medical agent, antibiotic, vitamin pills (multi-vitamin pills), amino acids, antithrombotic agents such as heparin, insulin, antitumor agent, painkillers, cardiotonic drug, intravenous anesthetic, antiparkinsonian agent, anti-ulcer agent, adrenal corticosteroid, an antiarrhythmic agent, electrolyte for correction, antiviral drugs, immunostimulant, and the like.

The outer cylinder 2 has the outer cylinder body part 21, the cylindrical (hollow) piercing needle mounting part 22 provided at the distal end portion of the outer cylinder body part 21, a flange 23 provided at a proximal end portion of the outer cylinder body part 21, and the piercing needle 6 whose proximal end portion is inserted into the piercing needle mounting part 22 and fixed thereto. The piercing needle 6 has the piercing needle tip 61 at its distal end. The proximal end portion of the piercing needle 6 is inserted into a hollow portion of the piercing needle mounting part 22 and fixed thereto. The inside of the piercing needle 6 communicates with an inner space 20 of the outer cylinder 2. The piercing needle 6 may be inserted into the hollow portion of the piercing needle mounting part 22 of the outer cylinder 2 molded in advance and fixed to the piercing needle mounting part 22 by means of an adhesive agent, thermal welding or the like. The piercing needle 6 may be fixed to the outer cylinder 2 by insert molding. In the case of the insert molding, by forming the outer cylinder 2 by molding a material, the piercing needle mounting part 22 has a cylindrical (hollow) configuration into which the piercing needle 6 has been inserted with the proximal end portion of the piercing needle 6 being inserted into the hollow portion of the piercing needle mounting part 22 and fixed thereto.

Figure 7:
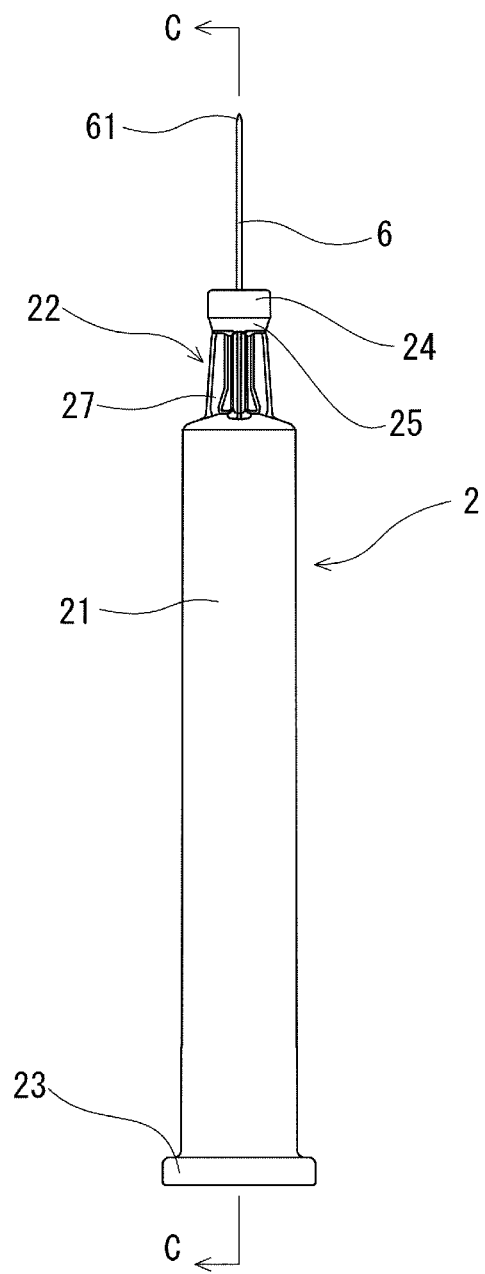
FIG. 7 is a front view of the outer cylinder for use in the prefilled syringe shown in FIGS. 1 and 2 and the syringe assembly shown in FIG. 3.
Figure 8:
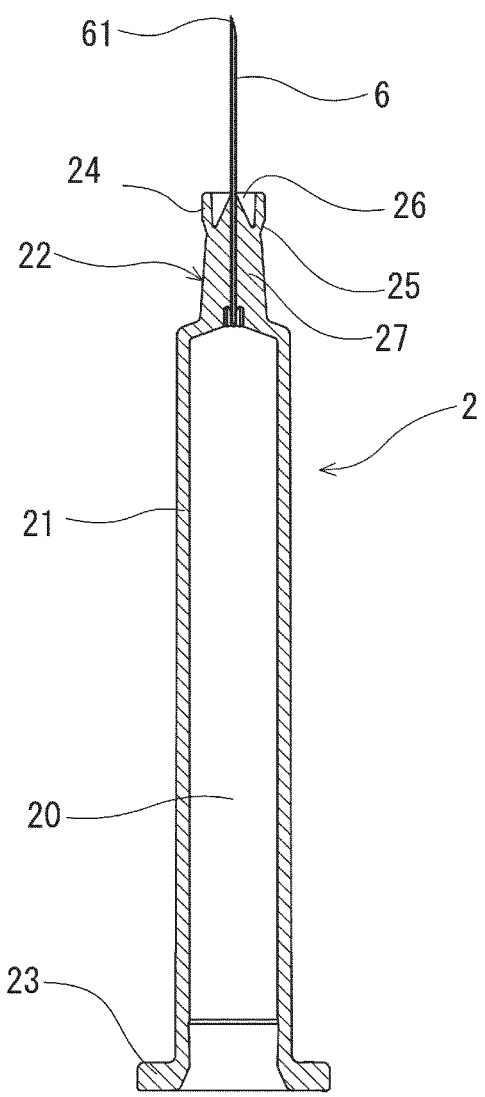
FIG. 8 is a sectional view taken along a line C-C of FIG. 7.
Figure 9:
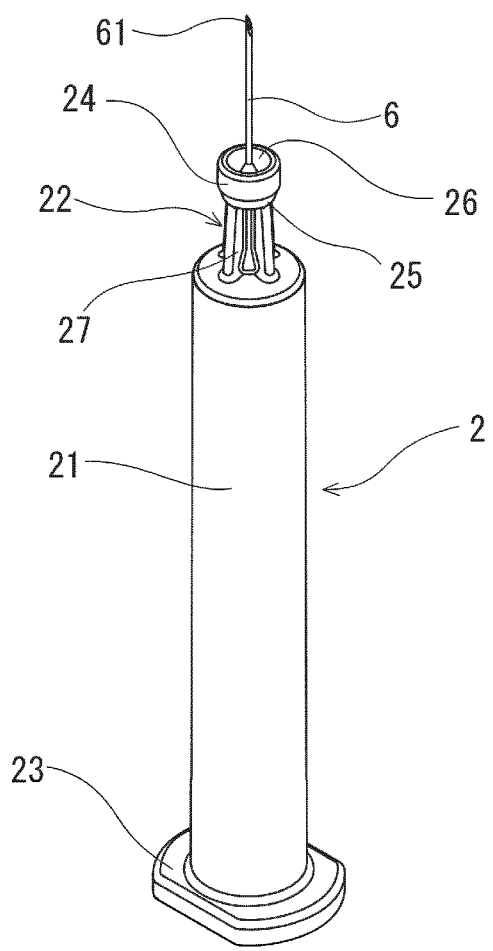
FIG. 9 is a perspective view of the outer cylinder shown in FIG. 7.

The outer cylinder 2 is transparent or semitransparent. The outer cylinder body part 21 is a substantially cylindrical portion which accommodates the gasket 4 liquid-tightly and slidably. The piercing needle mounting part 22 is a hollow and cylindrical part projecting forward from the distal end portion (shoulder portion) of the outer cylinder body part and having a smaller diameter than the outer cylinder body part. As shown in FIGS. 7 and 8, the piercing needle mounting part 22 has an annular head portion 24 provided at its distal end, a short-tapered diameter-reduced portion 25 which is provided at the proximal end of the annular head portion 24 and becomes shorter toward its proximal end in its diameter, and a connecting portion 27 connecting a proximal end portion of the tapered diameter-reduced portion 25 and the distal end portion of the outer cylinder body part 21 to each other. An annular concave portion is formed of the tapered diameter-reduced portion 25. In the annular head portion 24, there are formed a concave portion 26 recessed from a distal end surface of the annular head portion 24 toward its proximal end and a hollow conical portion which is positioned inside the concave portion 26 and has an apex at its distal end side. A plurality of grooves extended in the axial direction of the outer cylinder 2 is formed on an outer surface of the connecting portion 27. The annular concave portion may not be tapered, but may have a diameter-decreased configuration so that the annular concave portion is stepped from the proximal end of the annular concave portion 24. In addition, it is possible to omit the formation of the connecting portion 27 and directly connect the proximal end portion of the annular concave portion (tapered diameter-reduced portion 25) and the distal end portion of the outer cylinder body part 21 to each other. It is also possible to omit the formation of the concave portion 26 and the conical portion so as to shape the annular head portion 24 hollowly and columnarly (cylindrically).

Examples of a material for the outer cylinder 2 include resins such as polyester including polypropylene, polyethylene, polystyrene, polyamide, polycarbonate, polyvinyl chloride, poly-(4-methylpentene-1), acrylic resin, acrylonitrile-butadiene-styrene copolymer, and polyethylene terephthalate; cyclic olefin polymers, and cyclic olefin copolymers. Of these resins, the polypropylene and the cyclic polyolefin (for example, the cyclic olefin polymers, and the cyclic olefin copolymers) are preferable because these resins can be easily molded and is heat-resistant.

As the piercing needle 6, a hollow one having the piercing needle tip 61 at its distal end is used. As a material for forming the piercing needle 6, metals are normally used. Of metals, stainless steel is preferable.

As shown in FIGS. 1 and 2, the gasket 4 has a body part extended in substantially the same diameter and a plurality of annular ribs (Two annular ribs are formed in this embodiment. When two or more annular ribs are formed, the number thereof is not limited, provided that liquid tightness and slidability are satisfied) formed on the body part. The ribs liquid-tightly contact the inner surface of the outer cylinder 2. A distal end surface of the gasket 4 has a configuration corresponding to that of the inner surface of the distal end of the outer cylinder 2 to prevent the formation of a gap between both surfaces as much as possible when both surfaces contact each other.

As a material for the gasket 4, it is preferable to use elastic rubber (for example, isoprene rubber, butyl rubber, latex rubber, silicone rubber, and the like); and synthetic resin (for example, styrene elastomer such as SBS elastomer, SEBS elastomer, and the like and olefin elastomer such as ethylene-α-olefin copolymer elastomer).

The gasket 4 has a concave portion extended inward from its proximal end portion. The concave portion of the gasket 4 is female screw-shaped and engageable with a male screw portion formed on an outer surface of a projected portion 52 formed at a distal end portion of the plunger 5. Engagement between the female and male screw portions prevents the plunger 5 from being removed from the gasket 4. The plunger 5 may be removed from the gasket and mounted thereon when the prefilled syringe is used. The plunger 5 has the projected portion 52 projected forward cylindrically from a disk portion disposed at its distal end. A male screw which threadedly engages the concave portion of the gasket 4 is formed on an outer surface of the projected portion. The plunger 5 has a body part 51 cross-shaped and axially extended and a pressing disk portion 53 provided at its proximal end portion.

The seal cap 3 of the present invention for the outer cylinder is used by mounting the seal cap on the outer cylinder having the outer cylinder body part 21, the cylindrical piercing needle mounting part 22 provided at the distal end portion of the outer cylinder body part 21 and having the annular head portion 24 and the annular concave portion 25 formed at the proximal end of the annular head portion 24, and the piercing needle 6, having the piercing needle tip 61 at its distal end, whose proximal end portion is inserted into the piercing needle mounting part 22 and fixed thereto.

The seal cap 3 has the closed distal end part 31, the open proximal end part 32, the hollow part 30 having the piercing needle mounting part-accommodating part 35 accommodating the piercing needle mounting part 22 and the piercing needle accommodating part 34 continuous with the piercing needle mounting part-accommodating part 35, the pierceable part 33 into which the piercing needle tip 61 of the piercing needle 6 accommodated inside the piercing needle accommodating part 34 can be pierced, and a projected part 36 formed on the inner surface of the piercing needle mounting part-accommodating part 35. The polyparaxylylene coating 9 for restraining the piercing needle mounting part 22 of the outer cylinder 2 and the piercing needle mounting part-accommodating part 35 from sticking to each other is formed on the inner surface of the piercing needle mounting part-accommodating part 35. When the seal cap 3 is mounted on the piercing needle mounting part 22 of the outer cylinder 2, the piercing needle tip 61 is pierced into the pierceable part 33 of the seal cap 3 and sealed. Further the projected part 36 and the annular concave portion 25 of the piercing needle mounting part 22 of the outer cylinder 2 engage each other. In addition, the inner surface of the piercing needle mounting part-accommodating part 35 and the outer surface of the piercing needle mounting part 22 closely contact each other through the polyparaxylylene coating 9.

More specifically, the seal cap 3 has the projected part 36, formed on the inner surface thereof, which is located at a position distal from the open proximal end part 32 at a predetermined length. The projected part 36 has an apex 36a projected to a highest extent and an inclined portion (tapered portion) 36b which is extended from the apex 36a toward the distal end of the seal cap and becomes gradually lower in its projection height toward the distal end of the seal cap. In this embodiment, the projected part 36 is formed as an annular projected part. The inclined portion 36b is formed as a tapered portion in which the inner diameter of the piercing needle mounting part-accommodating part 35 decreases toward the distal end of the seal cap.

The inner diameter of the piercing needle mounting part-accommodating part 35 at the apex 36a is set a little smaller than the outer diameter of a distal end portion of the annular concave portion 25 of the piercing needle mounting part 22 of the outer cylinder 2. Thereby when the seal cap 3 is mounted on the piercing needle mounting part 22 of the outer cylinder 2, the projected part 36 and the annular concave portion 25 engage each other. In a state where the seal cap 3 is mounted on the piercing needle mounting part 22, the distal end side inclined portion 36b is extended toward the distal end of the seal cap beyond the annular concave portion 24. The inner diameter of the piercing needle mounting part-accommodating part 35 in the vicinity of at least the proximal end portion of the distal end side inclined portion 36b is set a little smaller than the outer diameter of the annular head portion 24 of the piercing needle mounting part 22 of the outer cylinder 2. Thereby when the seal cap 3 is mounted on the piercing needle mounting part 22 of the outer cylinder 2, the distal end side inclined portion 36b is pressed against the outer surface of the annular head portion 24 through the polyparaxylylene coating 9 and kept in close contact with the outer surface thereof. Thereby it is possible to reduce undesired removal of the seal cap 3 from the outer cylinder 2.

In the seal cap 3 of this embodiment, the inner diameter of the piercing needle mounting part-accommodating part 35 at the distal end portion of the distal end side inclined portion 36b is set a little smaller than the outer diameter of the annular head portion 24 of the piercing needle mounting part 22 of the outer cylinder 2. Thereby when the seal cap 3 is mounted on the piercing needle mounting part 22 of the outer cylinder 2, the inner surface of the distal end side inclined portion 36b is entirely pressed against the outer surface of the annular head portion 24 through the polyparaxylylene coating 9 and closely contacts the outer surface thereof. Thereby there is an increase in the area of the distal end side inclined portion 36b which is pressed against the outer surface of the annular head portion 24 through the polyparaxylylene coating 9 and closely contacts the outer surface thereof. Thereby it is possible to reduce undesired removal of the seal cap 3 from the outer cylinder 2 to a higher extent.

In the seal cap 3 of this embodiment, the projected part 36 is formed annularly along the inner surface of the piercing needle mounting part-accommodating part 35. Thus as compared with a case where the projected part 36 is intermittently formed on the inner surface of the piercing needle mounting part-accommodating part 35, there is an increase in the area of the distal end side inclined portion 36b which is entirely pressed against and closely contacts the outer surface of the annular head portion 24 through the polyparaxylylene coating 9. Thereby it is possible to reduce undesired removal of the seal cap 3 from the outer cylinder 2 to a higher extent. The projected part 36 may be intermittently formed on the inner surface of the piercing needle mounting part-accommodating part 35.

In the seal cap 3 of this embodiment, the projected part 36 further includes a proximal end side inclined portion 36c which extends from the apex 36a toward an open end (proximal end) of the seal cap and gradually decreases in its projection height toward the open end (proximal end) of the seal cap. Thereby in mounting the seal cap 3 on the piercing needle mounting part 22 of the outer cylinder 2, the apex 36a of the projected part 36 is capable of easily climbing over the annular head portion 24 of the piercing needle mounting part 22 from the distal end side of the annular head portion 24.

In this embodiment, the projected part 36 is formed as the annular projected part. The proximal end side inclined portion 36c is formed as the proximal end side tapered portion in which the inner diameter of the piercing needle mounting part-accommodating part 35 gradually increases toward the proximal end thereof. In the seal cap 3 of this embodiment, the proximal end side inclined portion (proximal end side tapered portion) 36c is shorter than the distal end side inclined portion (distal end side tapered portion) 36b and has a larger tapered angle than the distal end side inclined portion.

In the seal cap 3 of this embodiment, the piercing needle mounting part-accommodating part 35 has a linear portion 36d extended at a predetermined length (more specifically, to the proximal end portion of the piercing needle accommodating part 34) from a distal end portion of the distal end side inclined portion 36b of the projected part 36 toward the distal end of the seal cap. The inner diameter of the piercing needle mounting part-accommodating part 35 at the linear portion 36d is constant and a little smaller than the outer diameter of the annular head portion 24 of the piercing needle mounting part 22 of the outer cylinder 2. Thereby when the seal cap 3 is mounted on the piercing needle mounting part 22 of the outer cylinder 2, the linear portion 36d is pressed against the outer surface of the annular head portion 24 through the polyparaxylylene coating 9 and consequently closely contacts the outer surface thereof. The inner diameter of the piercing needle mounting part-accommodating part 35 at the linear portion 36d may be larger than the outer diameter of the annular head portion 24 of the piercing needle mounting part 22 of the outer cylinder 2. It is possible to omit the formation of the linear portion 36d and extend the distal end side inclined portion 36b to the proximal end portion of the piercing needle accommodating part 34.

The resistance of the outer cylinder 2 to the removal of the seal cap 3 therefrom is set to favorably 1.5N to 20N and more favorably 5 to 8N. Thereby it is possible to prevent undesired removal of the seal cap 3 from the outer cylinder 2, and to the contrary, it is possible to allow the seal cap 3 to easily remove from the outer cylinder 2 when the prefilled syringe 1 is used.

The inclination angle (taper angle) of the distal end side inclined portion 36b of the projected part 36 of the seal cap 3 is set to favorably 1 to 10 degrees and especially favorably one to six degrees. The projection height of the apex of the projected part 36 is set to favorably 0.1 to 0.5 mm and especially favorably 0.05 to 0.25 mm.

In this embodiment, the proximal end portion of the distal end side inclined portion 36b of the projected part 36 of the seal cap 3 is positioned on the periphery of the annular concave portion 24 of the piercing needle mounting part 22 of the outer cylinder 2. The inner diameter of the piercing needle mounting part-accommodating part 35 in the vicinity of at least the proximal end portion of the distal end side inclined portion 36b is set a little smaller than the outer diameter of the annular head portion 24. Therefore, the distal end side inclined portion 36b of the projected part 36 of the seal cap 3 is pressed against the outer surface of the annular concave portion 25 through the polyparaxylylene coating 9 and consequently closely contacts the outer surface thereof. Thereby it is possible to reduce undesired removal of the seal cap 3 from the outer cylinder 2 to a higher extent.

In this embodiment, the annular concave portion 25 consists of the tapered diameter-reduced portion which is provided at the proximal end of the annular head portion 24 and decreases toward the proximal end of the outer cylinder in its diameter. Thereby in removing the seal cap 3 from the outer cylinder 2, the projected part 36 of the seal cap 3 is expanded outward along the annular concave portion 25 and is capable of easily climbing over the annular head portion 24.

A portion of the distal end side inclined portion 36b, of the projected part 36 of the seal cap 3, which is pressed against and closely contacts the outer surface of the annular head portion 24 through the polyparaxylylene coating 9 is set to favorably 0.1 to 2.0 mm and more favorably 0.3 to 1.5 mm in the axial length of the annular head portion 24. Thereby it is possible to reduce undesired removal of the seal cap 3 from the outer cylinder 2 and restrain the resistance of the outer cylinder 2 to the removal of the seal cap 3 from becoming higher more than necessary.

Figure 10:
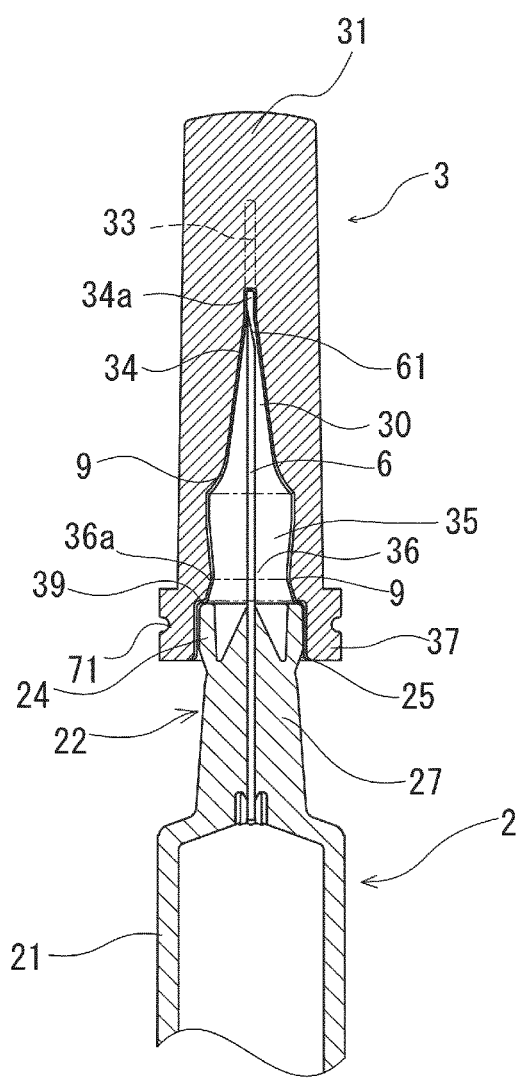
FIG. 10 is an explanatory view for explaining the action of the seal cap for use in the outer cylinder of the present invention.

In the seal cap 3 of this embodiment, the hollow part 30 has a piercing needle mounting part-introducing portion 38 which is formed in a range from the open proximal end part 32 of the seal cap 3 to the proximal end of the piercing needle mounting part-accommodating part 35 (projected part 36) and is extended in substantially the same inner diameter. The piercing needle mounting part-introducing portion 38 has an inner diameter a little larger than a maximum inner diameter of the piercing needle mounting part-accommodating part 35 and a little larger than the outer diameter of the annular head portion 24 of the piercing needle mounting part 22 of the outer cylinder 2. Therefore, in mounting the seal cap 3 on the piercing needle mounting part 22 of the outer cylinder 2, the piercing needle mounting part-introducing portion 38 functions as a portion for introducing the piercing needle mounting part 2 into the seal cap. The piercing needle mounting part-introducing portion 38 has an annular erect surface 39 erect toward the open proximal end part 32 at a boundary between the piercing needle mounting part-introducing portion and the proximal end of the piercing needle mounting part-accommodating part 35 (projected part 36). Thus when the distal end of the outer cylinder 2 is inserted into the piercing needle mounting part-introducing portion 38 of the seal cap 3, the piercing needle mounting part 22 of the outer cylinder 2 enters the piercing needle mounting part-introducing portion 38. Thereafter as shown in FIG. 10, an annular distal end surface of the annular head portion 24 of the piercing needle mounting part 22 contacts the annular erect surface 39. In this state, the piercing needle 6 becomes substantially parallel with the central axis of the seal cap 3 and has a state in which the piercing needle enters the small-diameter distal end portion 34a of the piercing needle accommodating part 34.

Provided that the inner diameter of at least the proximal end portion of the piercing needle mounting part-introducing portion 38 is larger than the outer diameter of the annular head portion 24 of the piercing needle mounting part 22 of the outer cylinder 2, the piercing needle mounting part-introducing portion 38 functions as the portion for introducing the piercing needle mounting part 22 into the seal cap. Thus unlike the above-described embodiment, the inner diameter of the piercing needle mounting part-introducing portion may become smaller toward its distal end. It is possible to omit the formation of the annular erect surface 39 at the piercing needle mounting part-introducing portion and gradually decrease the inner diameter of the piercing needle mounting part-introducing portion toward the proximal end of the piercing needle mounting part-accommodating part 35 (projected part 36). Thereby when the annular distal end surface of the annular head portion 24 of the piercing needle mounting part 22 enters the boundary between the proximal end of the piercing needle mounting part-accommodating part 35 (projected part 36) and the piercing needle mounting part-introducing portion, the piercing needle 6 becomes substantially parallel with the central axis of the seal cap 3 and has a state in which the piercing needle enters the small-diameter distal end portion 34a of the piercing needle accommodating part 34.

In the seal cap 3 of this embodiment, the proximal end of the piercing needle accommodating part 34 is positioned at the distal end of the linear portion 36d of the piercing needle mounting part-accommodating part 35 and becomes rapidly small toward its distal end in its inner diameter. The proximal end portion of the piercing needle accommodating part 34 is formed as an inwardly curved annular surface to prevent the piercing needle 6 from being pierced thereinto and securely guide the piercing needle toward its distal end. The body portion (central portion) of the piercing needle accommodating part is formed as a tapered portion which becomes gradually smaller toward its distal end in its diameter. A small-diameter distal end portion 34a which has an inner diameter a little larger than the outer diameter of the piercing needle 6 and is extended in substantially the same inner diameter is formed at the distal end of the piercing needle accommodating part.

As shown in FIG. 10, the seal cap of this embodiment is so constructed that in a state where the piercing needle mounting part 22 of the outer cylinder 2 is inserted into the seal cap and the annular distal end surface of the annular head portion 24 of the piercing needle mounting part 22 contacts the annular erect surface 39 of the piercing needle mounting part-introducing portion 38 of the seal cap 3, the piercing needle tip 61 of the piercing needle 6 enters the small-diameter distal end portion 34a of the piercing needle accommodating part 34 and does not reach the pierceable part 33. The pierceable part 33 is positioned distally (at distal end side) from the piercing needle mounting part-introducing portion 38. Exactly, the pierceable part is positioned distally from the small-diameter distal end portion 34a of the piercing needle accommodating part 34 and on an extension of the small-diameter distal end portion 34a. The configuration of the piercing needle accommodating part 34 is not limited to a specific one, provided that the piercing needle accommodating part is capable of accommodating the piercing needle 6. For example, the piercing needle accommodating part may be cylindrical.

Figure 6:
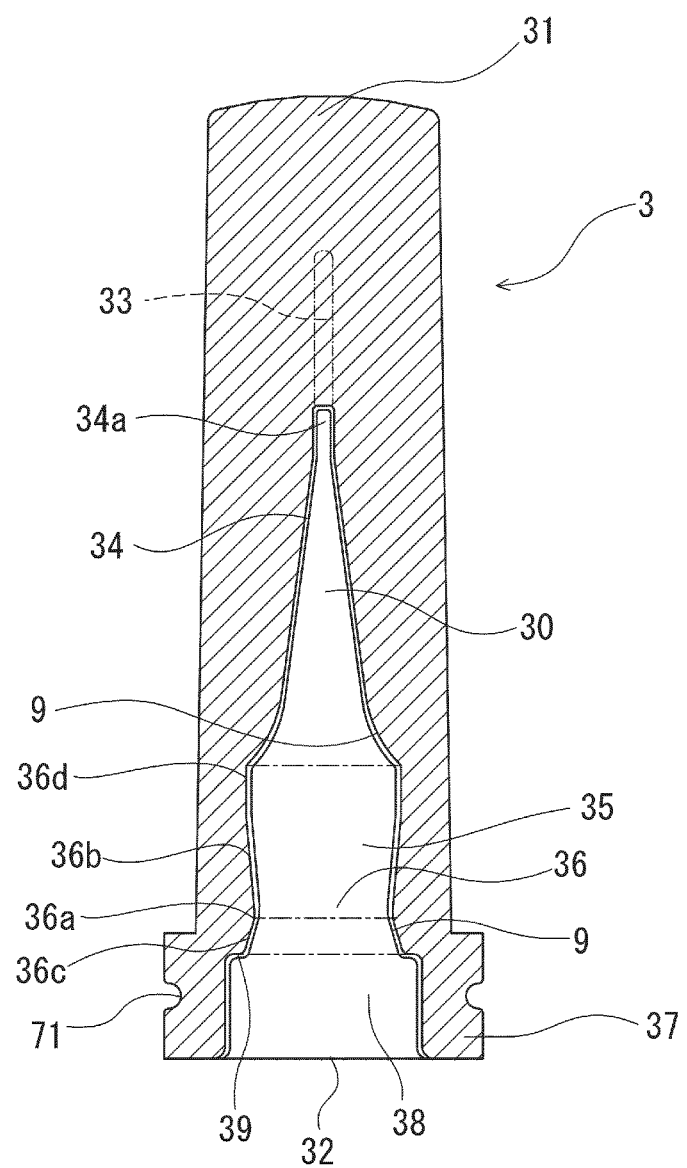
FIG. 6 is an enlarged sectional view taken along a line B-B of FIG. 4.

A gripping flange 37 is formed at the proximal end portion of the seal cap 3 by projecting the flange outward and annularly. An annular concave portion 71 is formed on the flange 37. The distal end position of the flange 37 is distal from the annular erect surface 39 of the hollow part 30 and in the vicinity of the apex 36a of the projected part 36 (in the case of the flange shown in FIG. 6, the distal end position of the flange is located at a position a little proximal toward the open proximal end part 32 from the apex 36a).

As a material for forming the seal cap 3, it is necessary to form at least the pierceable part 33 of an elastic material which allows the piercing needle to be pierced thereinto. As the elastic material which allows the piercing needle to be pierced into the pierceable part, it is preferable to use a thermoplastic elastomer, for example, a styrene elastomer such as an SBS elastomer, a SEB elastomer, and the like; an olefinic elastomer such as ethylene-olefin copolymer elastomer and the like. As the elastic material, butyl rubber, isoprene rubber, latex rubber, silicone rubber may be used.

In the seal cap 3 of this embodiment, at least the piercing needle mounting part-accommodating part 35 and the pierceable part 33 (in this embodiment, the entire seal cap) are formed of the elastic material which allows the piercing needle to be pierced thereinto. Therefore, when the seal cap 3 is mounted on the piercing needle mounting part 22 of the outer cylinder 2, the inner surface of the piercing needle mounting part-accommodating part 35 deforms elastically in conformity with the outer surface of the annular head portion 24 of the piercing needle mounting part 22. Thereby the inner surface of the piercing needle mounting part-accommodating part 35 and the outer surface of the annular head portion 24 of the piercing needle mounting part 22 closely contact each other to a higher extent through the polyparaxylylene coating 9. Thereby it is possible to decrease an undesired removal of the seal cap 3 from the outer cylinder 2 to a higher extent.

The seal cap 3 may be so formed that only the pierceable part 33 and the neighborhood thereof are formed of the above-described elastic material which allows the piercing needle to be pierced thereinto and that the outer peripheral portion of the pierceable part 33 and the neighborhood thereof are formed of a hard or semi-rigid material. As materials for forming the outer side of the seal cap, it is possible to list resins such as polyester including polypropylene, polyethylene, polystyrene, polyamide, polycarbonate, polyvinyl chloride, poly-(4-methylpentene-1), acrylic resin, acrylonitrile-butadiene-styrene copolymer, and polyethylene terephthalate; and cyclic polyolefin. It is possible to form at least the piercing needle mounting part-accommodating part of the seal cap 3 and the pierceable part thereof of the above-described elastic material which allows the piercing needle to be pierced thereinto and cover at least one portion of the outer peripheral portion of the piercing needle mounting part-accommodating part and the pierceable part with a covering member formed of the above-described hard or semi-rigid material.

The polyparaxylylene coating 9 for restraining the inner surface of the piercing needle mounting part-accommodating part 35 and the outer surface of the piercing needle mounting part 22 of the outer cylinder 2 from sticking to each other is formed on at least the inner surface of the piercing needle mounting part-accommodating part 35 of the seal cap 3. The polyparaxylylene coating 9 may be formed not entirely on the inner surface of the piercing needle mounting part-accommodating part 35, but at a portion of the inner surface thereof which closely contacts the outer surface of the piercing needle mounting part 22. The syringe assembly of present invention is particularly effective in a case where the seal cap 3 is formed of the thermoplastic elastomer and the outer cylinder 2 is formed of the cyclic polyolefin respectively.

In the seal cap 3 of this embodiment, the polyparaxylylene coating 9 is formed on the entire inner surface of the piercing needle accommodating part 34. Therefore, when the piercing needle tip 61 of the piercing needle 6 contacts the inner surface of the piercing needle accommodating part 34, the piercing needle does not stick to the inner surface thereof. Thereby in mounting the seal cap 3 on the piercing needle mounting part 22 of the outer cylinder 2, the piercing needle tip 61 of the piercing needle 6 which has entered the piercing needle accommodating part 34 is guided to the distal end (small-diameter distal end portion 34a) of the piercing needle accommodating part 34 without sticking to the inner surface of the piercing needle accommodating part 34 and is securely pierced into the pierceable part 33.

In the seal cap 3 of this embodiment, the polyparaxylylene coating 9 is formed entirely on the inner surface of the piercing needle mounting part-introducing portion 38. Thus when the piercing needle mounting part 22 enters the piercing needle mounting part-introducing portion 38, it does not occur that the outer surface of the piercing needle mounting part 22 sticks to the inner surface of the piercing needle mounting part-introducing portion 38. Thereby it is possible to smoothly mount the seal cap 3 on the piercing needle mounting part 22 of the outer cylinder 2.

Figure 3:
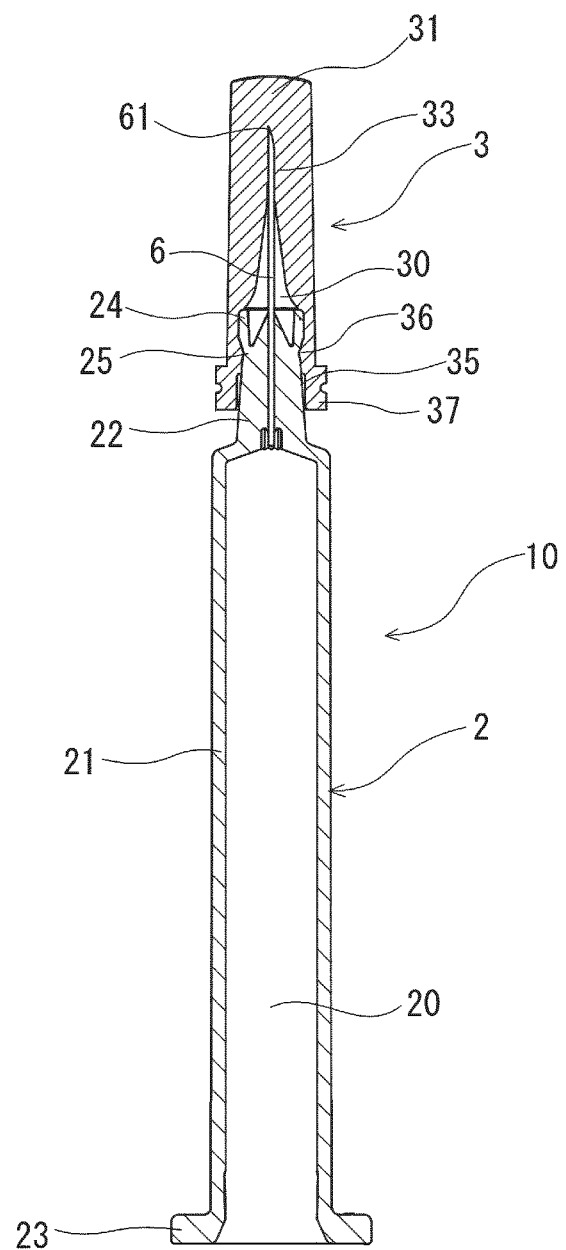
FIG. 3 is an enlarged sectional view of a syringe assembly of the present invention for use in the prefilled syringe shown in FIGS. 1 and 2.
Figure 4:
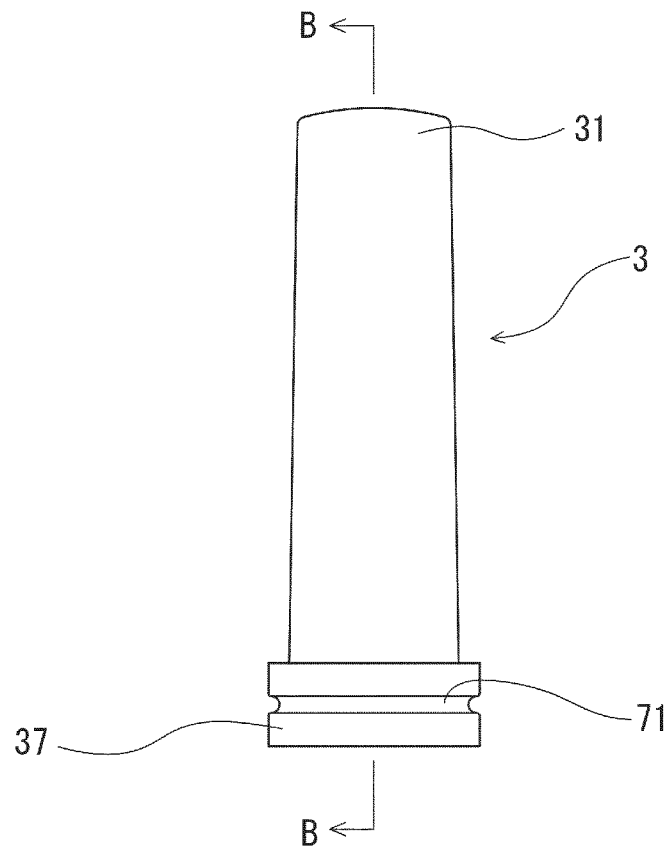
FIG. 4 is an enlarged front view of a seal cap for an outer cylinder for use in the prefilled syringe shown in FIGS. 1 and 2 and the syringe assembly shown in FIG. 3.
Figure 5:
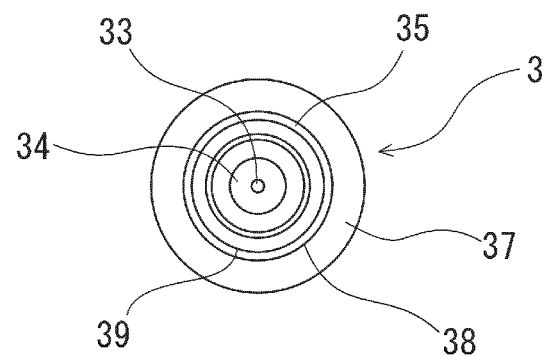
FIG. 5 is a bottom view of the seal cap for the outer cylinder shown in FIG. 4.

As shown in FIG. 3, in the syringe assembly 10 of the present invention, the seal cap 3 is mounted on the distal end portion (piercing needle mounting part 22) of the outer cylinder 2; the piercing needle tip 61 of the piercing needle 6 is pierced into the pierceable part 33 of the seal cap 3 and is sealed liquid-tightly, the annular concave portion 25 of the piercing needle mounting part 22 and the projected part 36 formed on the inner surface of the piercing needle mounting part-accommodating part 35 engage each other, and the inner surface of the piercing needle mounting part-accommodating part 35 and the outer surface of the piercing needle mounting part 22 are kept in close contact with each other through the polyparaxylylene coating 9.

In the syringe assembly 10, the inner surface of the piercing needle mounting part-accommodating part 35 and the outer surface of the piercing needle mounting part 22 are kept in close contact with each other through the polyparaxylylene coating 9. Thus in a case where the syringe assembly is stored with the seal cap 3 being mounted on the outer cylinder 2 and even in a case where the syringe assembly undergoes high-pressure steam sterilization or ethylene oxide gas sterilization which subjects the syringe assembly to the receipt of the application of a pressure load, it is possible to restrain the inner surface of the piercing needle mounting part-accommodating part 35 and the outer surface of the piercing needle mounting part 22 from sticking to each other. Similarly, in the prefilled syringe 1 of the present invention, the inner surface of the piercing needle mounting part-accommodating part 35 and the outer surface of the piercing needle mounting part 22 are kept in close contact with each other through the polyparaxylylene coating 9. Thus in a case where the syringe assembly is stored with the seal cap 3 being mounted on the outer cylinder 2 and even in a case where the syringe assembly undergoes the high-pressure steam sterilization or the ethylene oxide gas sterilization which subjects the syringe assembly to the receipt of the application of a pressure load, it is possible to restrain the inner surface of the piercing needle mounting part-accommodating part and the outer surface of the piercing needle mounting part 22 from sticking to each other.

Although in the above-described embodiment, the polyparaxylylene coating 9 is formed on the inner surface of the piercing needle mounting part-accommodating part 35, the portion where the polyparaxylylene coating is formed is not limited thereto, but may be formed on the outer surface of the piercing needle mounting part of the outer cylinder. Further, the polyparaxylylene coating may be formed on both the inner surface of the piercing needle mounting part-accommodating part and on the outer surface of the piercing needle mounting part.

The poly-para-xylylene shown by the following chemical formula can be preferably used.

[Chemical formula 1]

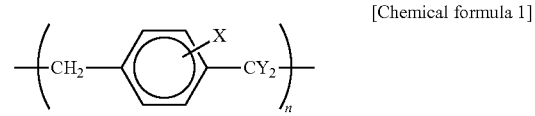

(X:H, Cl or CH$_3$, Y:H or F)

In the present invention, it is possible to use poly(para-xylylene) whose aromatic ring is not substituted with a functional group and poly(para-xylylene) in which the functional group is introduced into the aromatic ring or the methylene group. For example, it is possible to use any of poly(chloro-para-xylylene) in which the aromatic ring is substituted with chlorine, polymethyl-para-xylylene in which the aromatic ring is substituted with a methyl group, and poly-fluoro-para-xylylene in which the methylene group is substituted with fluorine. It is possible to use not only a homopolymer consisting of the poly(para-xylylene), but also a copolymer composed of a para-xylylene monomer and a monomer copolymerizable therewith. It is especially preferable to use the poly(para-xylylene) and the poly(chloro-para-xylylene) in which the aromatic ring is not substituted with the functional group. The polyparaxylylene coating 9 may be formed of a single layer of the poly-paraxylylene or that of the copolymer or formed of a multilayer of the poly-paraxylylene and/or the copolymer.

In the present specification, the poly-paraxylylene means not only the poly-paraxylylene in which the aromatic ring is not substituted with the functional group, but also the pol-yparaxylylene shown by the chemical formula 1.

It is preferable that the poly-para-xylylene to be used in the present invention is a laminated film formed by polymerizing the para-xylylene monomers obtained by thermally decomposing a para-xylylene dimer, shown by the chemical formula 1, which is used as a raw material. The laminated film formed in the above-described manner does not generate pin holes and is stable in its thickness. The thickness of the poly-para-xylylene of the polyparaxylylene coating is set to favorably 1 μm to 10 μm and especially favorably 2 μm to 8 μm.

The polyparaxylylene coating forming process is described below.

It is preferable to form a film consisting of the poly-para-xylylene on the inner surface of the seal cap by polymerizing the poly-para-xylylene monomers shown by the chemical formula 1 with one another. It is also preferable to form a thin film of the poly-para-xylylene in the polyparaxylylene coating forming process by carrying out a chemical vapor deposition method (C.V.D. method), a sputtering method, an ion plating method or the like. By chemically depositing the para-xylylene monomers on the inner surface of the seal cap, the poly-para-xylylene monomers are polymerized simultaneously with the formation of the polyparaxylylene coating. Therefore, the polyparaxylylene coating is formed uniformly on the inner surface of the seal cap by the chemical deposition.

A polyparaxylylene coating forming apparatus having a para-xylylene dimer vaporizing chamber, a para-xylylene dimer pyrolysis chamber, and a poly-para-xylylene deposition chamber is used. In a polyparaxylylene coating forming method, after the seal cap is supplied to the deposition chamber, the pressure inside the apparatus is reduced to 5 to 50 mTorr and preferably 10 to 30 mTorr to vaporize the para-xylylene dimer which is the material of the polyparaxylylene coating at 100 to 200 degrees C. in the vaporizing chamber. Thereafter the para-xylylene monomers obtained by thermally decomposing the para-xylylene dimer heated at 650 to 700 degrees C. in the pyrolysis chamber is flowed into the deposition chamber. Upon contact between the para-xylylene monomers and the seal cap, the para-xylylene monomers polymerize with one another at the interface therebetween to form the polyparaxylylene coating. The polyparaxylylene coating obtained in the above-described manner is excellent in its chemical resistance and gas barrier property, is formed uniformly and continuously, and does not generate pin holes. The thickness of the poly-para-xylylene layer can be controlled according to a pressure reduction degree, the temperature of the vaporizing chamber, and a deposition period of time.

The polyparaxylylene coating forming process may be performed by thinly applying a liquid material of the poly-para-xylylene or paste thereof to the inner surface of the seal cap 3 to form a thin film thereon. The polyparaxylylene coating forming process may be also performed by fusing the film or the thin film consisting of the poly-para-xylylene to the inner surface of the seal cap thermally, by high frequency welding or by pasting the film or the thin film to the inner surface of the seal cap with an adhesive agent.

EXAMPLES

Example 1

By using thermoplastic elastomer (TPE) as the material for the seal cap and monochloro-para-xylylene dimer [dichloro-(2,2)-paracyclophane] (commercial name: dix-c produced by Daisan Kasei Co., Ltd.) as the material for the poly-para-xylylene, a polyparaxylylene coating was formed on the inner surface of the seal cap in the region from at least the open portion of the seal cap to a position distal at a predetermined length from the open portion. More specifically, by using a chemical vapor deposition apparatus (model: S, capacity of tumbler: 25 L, produced by Daisan Kasei Co., Ltd.) constructed of a vaporizing chamber, a pyrolytic furnace, and a deposition chamber, a film of poly(chloro-para-xylylene) was formed on the inner and outer surfaces of the seal cap made of the thermoplastic elastomer (specifically, styrene elastomer).

More specifically, after dichloro-(2,2)-paracyclophane which is a dimer was supplied to the vaporizing chamber, the pressure inside the apparatus was adjusted to a vacuum degree of 30 mTorr. Thereafter the dichloro-(2,2)-paracyclophane which is the dimer was heated to 150 to 170 degrees C. to sublime the dichloro-(2,2)-paracyclophane which is the dimer supplied into the vaporizing chamber. Subsequently the dimer was passed through the pyrolytic furnace having a temperature of 650 to 690 degrees C. to thermally decompose the dimer into monomers. Finally, the monomers were induced into the deposition chamber (room temperature) having a tumbler containing 500 seal caps. Thereafter the monomers were treated for 25 minutes to form a poly-para-xylylene layer. In this manner, seal caps having the polyparaxylylene coating of the present invention formed thereon were prepared. The tumbler was rotated at 2 rpm while the seal caps were being stirred to form a sticking restraining layer on the seal caps. After the polyparaxylylene coating was formed, 30 seal caps were arbitrarily selected to measure the thickness of the film formed on the inner surface of each seal cap. As a result, the average thickness of the films was 1 μm.

Example 2

Except that the period of time required to treat the monomer introduced into the chamber was 125 minutes, seal caps each having the polyparaxylylene coating of the present invention formed on the inner surface thereof were prepared in a manner similar to that of the example 1. After the polyparaxylylene layer was formed, 30 seal caps were arbitrarily selected to measure the thickness of the film formed on the inner surface of each seal cap. As a result, the average thickness of the films was 5 μm.

Example 3

Except that thermoplastic elastomer (specifically, styrene elastomer) obtained by doping silicone oil was introduced into the vaporizing chamber as the material for seal caps, seal caps having the polyparaxylylene coating of the present invention formed on the inner surface thereof were prepared in a manner similar to that of the example 1. Thereafter 30 seal caps were arbitrarily selected to measure the thickness of the film formed on the inner surface of each seal cap. As a result, the average thickness of the films was 1 μm.

Example 4

Except that thermoplastic elastomer (specifically, styrene elastomer) obtained by doping aliphatic amide (specifically, stearic acid amide) was introduced into the vaporizing chamber as the material for the seal cap and that monochloro-para-xylylene dimer [1,4-bis(dichloromethyl)benzene] (commercial name: dix-d produced by Daisan Kasei Co., Ltd.) was used as the material for the poly-para-xylylene, seal caps each having the polyparaxylylene coating of the present invention formed on the inner surface thereof were prepared in a manner similar to that of the example 2. Thereafter 30 seal caps were arbitrarily selected to measure the thickness of the film formed on the inner surface of each seal cap. As a result, the average thickness was 5 μm.

Comparison Example 1

Except that the polyparaxylylene coating was not formed, seal caps were prepared in a manner similar to that of the example 1.

Comparison Example 2

Except that instead of forming the polyparaxylylene coating, a liquid coating agent (commercial name: Dow Corning Toray Co., Ltd./MDX4-4159) containing reactive silicone oil as its main component was polymerized (including crosslinking) to form a film on the inner surface of each seal cap at a normal temperature or by heating the liquid coating agent, 100 seal caps having a silicone polymerized film formed on the inner surface thereof were prepared in a manner similar to that of the example 1. Thereafter 30 seal caps were arbitrarily selected to measure the thickness of each silicone polymerized film formed on the inner surface of each seal cap. As a result, the average thickness was 1 µm.

Experiment 1: Removal Strength Test

After silicone was applied to the needle tip of a piercing needle, seal caps were mounted on outer cylinders respectively at a predetermined position thereof. An internal pressure inside the seal cap rises when the seal cap is mounted on the outer cylinder. Thus a gap was formed between the outer cylinder and the seal cap by deforming a portion of the seal cap in the vicinity of the open portion thereof so as to release the internal pressure. After the seal cap was mounted on the outer cylinder, the seal cap and the outer cylinder were subjected to autoclave treatment (123 degrees C., 85 minutes). After a hook was put on the distal end of the seal cap, a flange of the outer cylinder was fixed to conduct a tensile test by using an autograph (load cell MAX100N). In this manner, the removal strength of the seal cap was measured. The test results were as shown in table 1.

It is preferable that the removal strength is low. It could be confirmed that the seal caps of the examples had low removal strength and an excellent sticking restraining effect.

Experiment 2: Sterility Test

After BI bacteria ($10^6$CFU/ml) were enclosed in the space formed of the outer cylinder and the cap, a seal cap was mounted on an outer cylinder at a predetermined position thereof similarly to the experiment 1. After the seal cap was mounted on the outer cylinder, each outer cylinder mounted the cap was subjected to autoclave treatment (123 degrees C., 10 minutes) by using a sterile pack. After the syringe assembly was subjected to sterilization, culture medium treatment was performed for 7 days. Results shown in table 1 were obtained.

The mark of ○ shows that the BI bacteria could be sterilized (all the bacteria were killed).

The mark of x shows that the BI bacteria could not be sterilized (none of the bacteria were killed).

It could be confirmed that the seal caps and the syringe assemblies of the examples had autoclave sterilizing performance.

Experiment 3: Pressure-Resistant Test

Based on "air tightness" described in JIS T 3210 (revised on 2011 Jul. 29), a pressure-resistant test was conducted. After a sufficient amount of water was wiped off from each outer cylinder, water was drawn into the outer cylinder to the level of ¾ thereof. After each outer cylinder was sealed with a seal cap, the pressure-resistant performance of each seal cap was measured by applying a pressure of 400 kPa to each pusher. Results were as shown in table 1.

The mark of ○ shows that seal cap was pressure-resistant (not leaked).

The mark of x shows that seal cap was not pressure-resistant (leaked).

It could be confirmed that the seal caps of the examples had a sufficiently high pressure resistance.

Experiment 4: Piercing Resistance Test

After silicone was applied to the needle tip of each piercing needle, seal caps were mounted on outer cylinders respectively at a predetermined position thereof. After the seal cap was mounted on the outer cylinder, the outer cylinders mounted the cap were subjected to autoclave treatment (123 degrees C., 85 minutes). After the seal caps were removed from the outer cylinders respectively, the piercing resistance of each seal cap to silicone rubber (t=0.5 mm) was measured by using an autograph. The seal cap having a low piercing resistance is preferable. The results were as shown in table 1. It could be confirmed that the needle tips pierced into the seal caps of the examples respectively had a sufficiently high piercing property.

Experiment 5: Moisture Transpiration Test

A test was conducted on water loss of "pharmaceutical preparation packaged by semipermeable container" described in the stability testing guidelines (2003 Jun. 3 Pharmaceutical Affairs Bureau Notification0603001) of drug with new active ingredients. The results were as shown in table 1.

The mark of ○ shows that syringe assemblies satisfied the function demanded as a medical agent container.

The mark of x shows that syringe assemblies did not satisfy the function demanded as the medical agent container. It could be confirmed that the seal caps of the examples had a sufficiently high pressure resistance.

TABLE 1

| | Removal strength test | Sterility test | Pressure-resistant test | Piercing resistance test | Moisture transpiration test |
|---|---|---|---|---|---|
| Example 1 | 8 N | ○ | ○ | 0.14 N | ○ |
| Example 2 | 7 N | ○ | ○ | 0.15 N | ○ |
| Example 3 | 7 N | ○ | ○ | 0.15 N | ○ |
| Example 4 | 8 N | ○ | ○ | 0.15 N | ○ |
| Comparison example 1 | 22 N | ○ | ○ | 0.14 N | ○ |
| Comparison example 2 | 21 N | ○ | ○ | 0.15 N | ○ |

Embodiments of a packaging body, shown in the drawings, which accommodates a plurality of the syringe assemblies of the present invention are described below by using FIGS. 11 through 15.

A prefilled syringe assembly packaging body 100 of the present invention accommodating a plurality of syringe assemblies which can be or is subjected to sterilization has a container body 102 whose upper surface is open and which has shape retainability, an outer cylinder holding member 104 capable of holding a plurality of syringe assemblies 10 accommodated inside the container body 102, a plurality of the syringe assemblies 10 held by the outer cylinder holding member 104, and a sheet-shaped lid member 103 which airtightly seals the open upper surface of the container body 102 and is peelable from the container body.

The prefilled syringe assembly packaging body 100 of the present invention can be or is subjected to sterilization. As a sterilization method, the high-pressure steam sterilization, radiation or electron beam sterilization, and the ethylene oxide gas sterilization are used.

Figure 11:
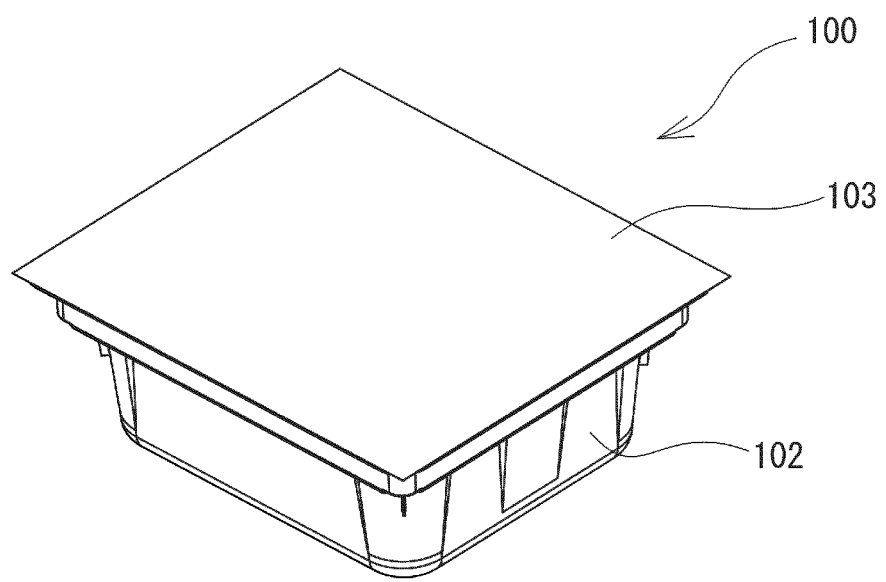
FIG. 11 is a perspective view of a syringe assembly packaging body of the present invention.
Figure 12:
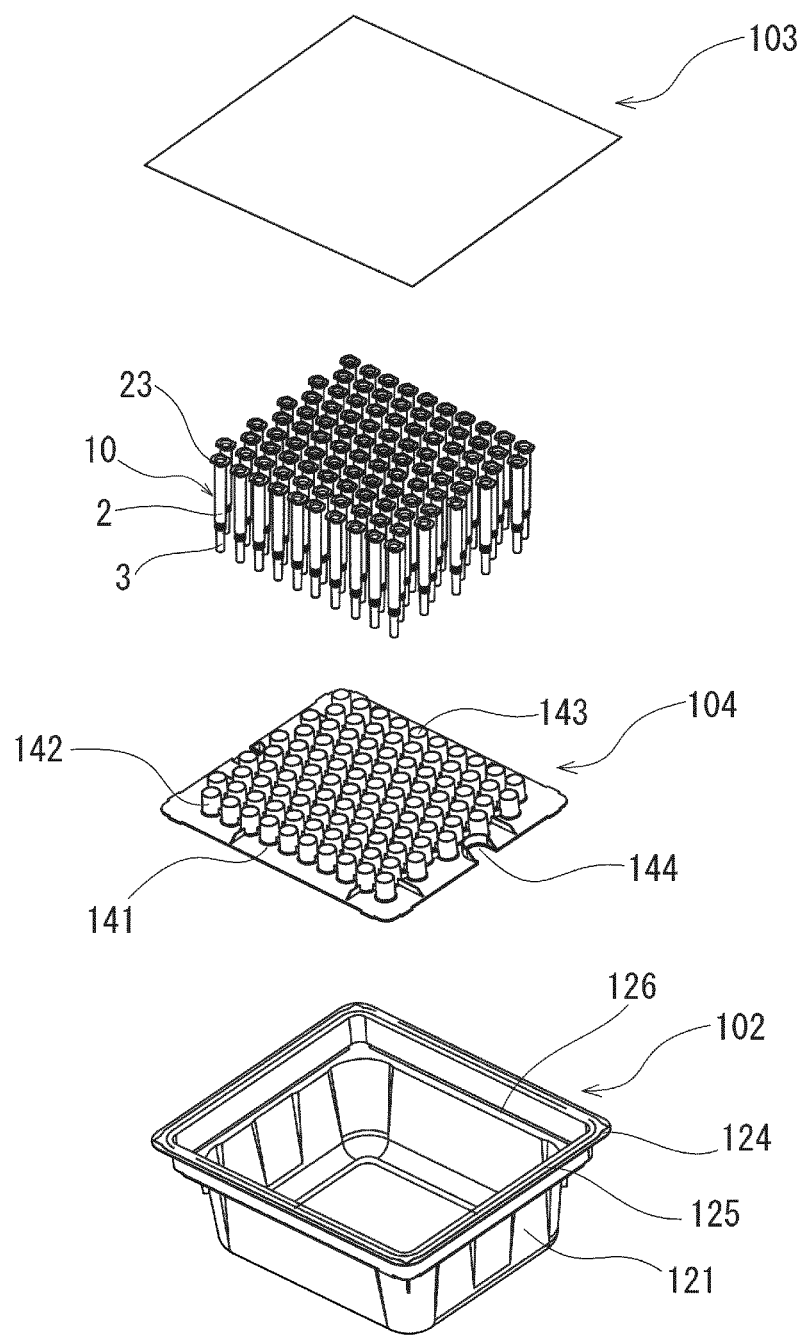
FIG. 12 is an explanatory view for explaining an inner form of the syringe assembly packaging body shown in FIG. 11.
Figure 13:
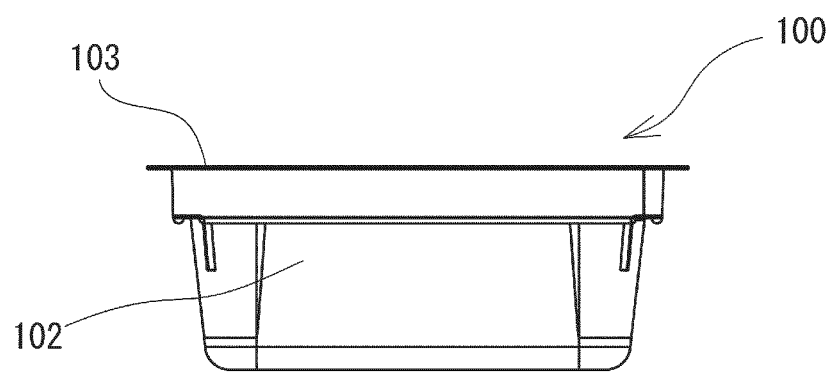
FIG. 13 is a front view of the syringe assembly packaging body shown in FIG. 11.
Figure 14:
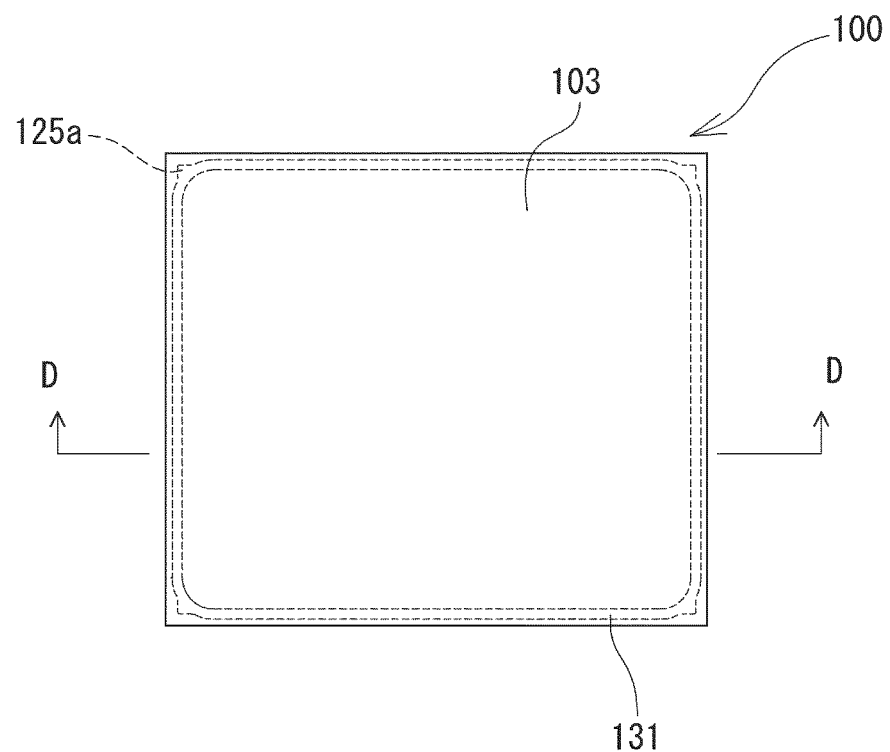
FIG. 14 is a plan view of the syringe assembly packaging body shown in FIG. 13.
Figure 15:
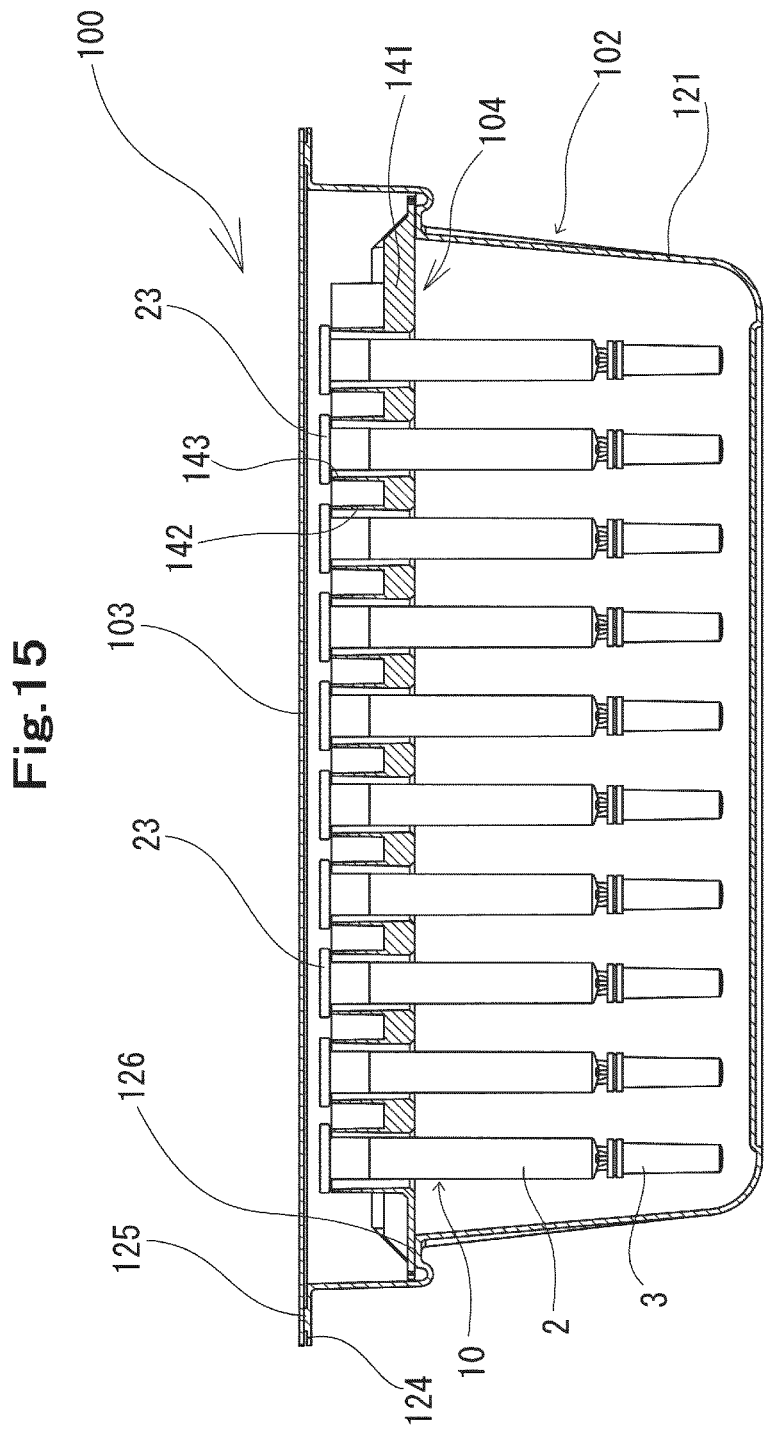
FIG. 15 is an enlarged sectional view taken along a line D-D of FIG. 14.

As shown in FIGS. 11, 12 and 15, the prefilled syringe assembly packaging body 100 of the present invention has the container body 102, the outer cylinder holding member 104 capable of holding a plurality of syringe assemblies 10, a plurality of the syringe assemblies 10 held by the outer cylinder holding member 104, and the sheet-shaped lid member 103 which airtightly seals the open upper surface of the container body 102 and is peelable therefrom. The packaging body 100 further includes an air-permeable part, having bacteria impermeability and sterilizing gas permeability, which is provided on the container body 102 or on the sheet-shaped lid member 103.

As shown in FIGS. 11 through 15, the container body 102 is tray-shaped and has strength and shape retainability to some extent and a predetermined depth. The container body 102 has a body part 121, an outer cylinder holding member-holding portion 126, formed at an upper portion of the body part 121, for holding a peripheral portion of the outer cylinder holding member 104 which holds a plurality of the syringe assemblies 10, and an annular flange 124 formed at the opening of the upper surface of the container body.

An annular heat-sealing convex portion 125 is formed on the upper surface of the annular flange 124 to fix the sheet-shaped lid member 103 to the heat-sealing convex portion 125. The outer cylinder holding member-holding portion 126 is provided at a position which is on the bottom side of a predetermined length with respect to the flange 124. In the container body 102 of a first embodiment, the outer cylinder holding member-holding portion 126 is formed as an annular stepped portion so that the peripheral portion of the outer cylinder holding member 104 which holds a plurality of the syringe assemblies 10 can be placed thereon.

It is preferable that the container body 102 has shape retainability and rigidity to some extent. To respond to the high-pressure steam sterilization, it is desirable to use a thermoplastic material having heat resistance (not less than 120 degrees C.). As materials having the shape retainability and the rigidity to some extent, heat resistance, and thermoplasticity, it is possible to exemplify polyolefin such as polypropylene and polyethylene, vinyl chloride resin, polystyrene/polypropylene resin, polyethylene/ionomer (for example, ethylene-based, styrene-based, fluorine-based)/polyethylene, polyester resin (for example, polyethylene terephthalate, polybutylene terephthalate, and amorphous polyethylene terephthalate), and PP/EVOH/PP (laminate) are listed. In this case, the thickness of the container 102 is set to favorably 0.05 to 4.00 mm and especially favorably 1.00 to 2.00 mm.

It is possible to subject the container body 102 to radiation sterilization or electron beam sterilization. In this case, it is desirable to use radiation-resistant material. As the radiation-resistant material (for example, radiation-resistant polyolefin), it is possible to use polyolefin (for example, polypropylene, polyethylene) to which radiation resistance has been imparted by adding hindered amine, an antioxidant, a nucleating agent, and the like. As the hindered amine, bis(2,2,6,6-tetramethylpiperidyl)sebacate, bis(2,2,6,6-tetramethylpiperidyl)adipate, bis(2,2,6,6-tetramethylpiperidyl)fumarate are exemplified. As the antioxidant, 1,1,3-tris (2-methyl-hydroxy-5-t-butylphenyl)butane, tris(3,5-di-T-butyl-4-hydroxybenzyl)isocyanurate, tetrakis(methylene-3-(3,5-di-t-butyl-4-hydroxyphenyl)propionate)methane are exemplified. As the nucleating agent, 1,3,2,4-dibenzylidene sorbitol and 1,3.2,4-di(p-methyl benzylidene)sorbitol are exemplified.

As shown in FIGS. 12 and 15, the outer cylinder holding member 104 capable of holding a plurality of the syringe assemblies 10 has a substrate part 141 and a plurality of cylindrical parts 142 projecting upward from the substrate part 141. An outer cylinder holding open portion 143 is formed inside each tubular part 142. A gripping cut-out 144 is formed on sides of the substrate part 141. The inner diameter of the tubular part 142 and that of the outer cylinder holding open portion 143 are set larger than the outer diameter of a maximum diameter portion of the syringe assembly 10 held by the outer cylinder holding member. It is impossible for the flange 23 of the syringe assembly 10 held by the outer cylinder holding member to pass through the tubular part 142 and the outer cylinder holding open portion 143.

Therefore, as shown in FIG. 15, the syringe assembly 10 passes through the cylindrical part 142, and the flange 23 of the syringe assembly 10 is hung by the outer cylinder holding open portion 143. As shown in FIG. 15, the lower end (the distal end of the seal cap 3) of the syringe assembly 10 held by the outer cylinder holding member 104 does not contact the bottom surface of the container body 102. In other words, the bottom surface of the container body 102 and the lower end (distal end of the seal cap 3) of the syringe assembly 10 held by the outer cylinder holding member 104 are spaced away from each other so that the space therebetween does not inhibit the circulation of water vapor. It is desirable that a material for forming the outer cylinder holding member 104 has heat resistance (not less than 120 degrees C.) so that the outer cylinder holding member is capable of responding to the high-pressure steam sterilization.

It is desirable that the sheet-shaped lid member 103 has a property of not allowing fine particles such as bacteria and virus to permeate there through to perform the high-pressure steam sterilization or the ethylene oxide gas sterilization and has a sterilizing gas-permeable property of allowing a sterilizing gas such as water vapor and ethylene oxide gas to permeate therethrough. It is preferable that the sheet-shaped lid member 103 can be heat-sealed to the container body 102. For example, it is possible to suitably use nonwoven cloth made of synthetic resin for the sheet-shaped lid member. More specifically, it is possible to use nonwoven cloth, known as Tyvek (registered trademark), which is made of a synthetic resin material such as polyolefin and a porous film made of synthetic resin for the sheet-shaped lid member.

The peripheral portion of the sheet-shaped lid member 103 is peelably heat-sealed to the heat-sealing convex portion 125 formed on the annular flange 124 of the container body 102. In the first embodiment, the outer edge of the sheet-shaped lid member 103 is not heat-sealed to the annular flange 124 of the container body 102 to easily peel the sheet-shaped lid member from the container body. A projected portion 125*a* formed at each corner of the heat-sealing convex portion 125 functions as a peeling starting portion. The thickness of the sheet-shaped lid member 103 is set to favorably 0.05 to 1.00 mm and more favorably 0.10 to 0.50 mm.

In the first embodiment, the air-permeable part is provided on the sheet-shaped lid member 103. The air-permeable part-forming position is not limited to the sheet-shaped lid member, but may be formed on the container body 102.

In the syringe assembly 10 accommodated inside the syringe assembly packaging body 100, the inner surface of the piercing needle mounting part-accommodating part 35 and the outer surface of the piercing needle mounting part 22 are kept in close contact with each other through the polyparaxylylene coating 9. Thus in a case where the prefilled syringe assembly packaging body 100 is stored with the seal cap 3 being mounted on the outer cylinder 2 and even in a case where the prefilled syringe assembly packaging body 100 undergoes the high-pressure steam sterilization or the ethylene oxide gas sterilization which subjects the syringe assembly to the receipt of the application of a pressure load, it is possible to restrain the inner surface of the piercing needle mounting part-accommodating part 35 and the outer surface of the piercing needle mounting part 22 from sticking to each other.

INDUSTRIAL APPLICABILITY

The syringe assembly of the present invention is constructed as described below.

(1) A syringe assembly comprising an outer cylinder having an outer cylinder body part, a cylindrical piercing needle mounting part provided at a distal end portion of said outer cylinder body part, and a piercing needle which has a piercing needle tip at a distal end thereof and whose proximal end portion is inserted into said piercing needle mounting part and fixed thereto and a seal cap mounted on said outer cylinder, wherein said seal cap has a closed distal end part, an open proximal end part, a piercing needle mounting part-accommodating part positioned at a side distal from said open proximal end part and accommodating a distal end portion of said piercing needle mounting part, a hollow part continuous with a distal end of said piercing needle mounting part-accommodating part and having a piercing needle accommodating part accommodating said piercing needle, and a pierceable part into which said piercing needle tip of said piercing needle accommodated inside said piercing needle accommodating part is pierceable, a polyparaxylylene coating is provided on an inner surface of said piercing needle mounting part-accommodating part of said seal cap or/and on an outer surface of said piercing needle mounting part of said outer cylinder, said seal cap is mounted on said outer cylinder; said piercing needle tip is pierced into said pierceable part of said seal cap; and said inner surface of said piercing needle mounting part-accommodating part of said seal cap and said outer surface of said piercing needle mounting part of said outer cylinder are kept in close contact with each other through said polyparaxylylene coating.

The syringe assembly of the present invention has the polyparaxylylene coating. The inner surface of the piercing needle mounting part-accommodating part and the outer surface of the piercing needle mounting part of the outer cylinder are kept in close contact with each other through the polyparaxylylene coating. Thus in a case where the syringe assembly is stored with the seal cap being mounted on the outer cylinder and even in a case where the syringe assembly undergoes the high-pressure steam sterilization or the ethylene oxide gas sterilization which subjects the syringe assembly to the receipt of the application of a pressure load with the seal cap being mounted on the outer cylinder, it is possible to prevent the inner surface of the seal cap and the outer surface of the distal end portion of the outer cylinder from sticking to each other and thus prevent the seal cap from being removed from the outer cylinder.

The above-described embodiments may be constructed as described below.

(2) A syringe assembly according to the above (1), wherein said piercing needle mounting part of said outer cylinder has an annular head portion and an annular concave portion formed at a proximal end of said annular head portion; said piercing needle mounting part-accommodating part of said seal cap has a projected part formed on an inner surface thereof; and said annular concave portion of said piercing needle mounting part and said projected part formed on said inner surface of said piercing needle mounting part-accommodating part engage each other and closely contact each other through said polyparaxylylene coating.

(3) A syringe assembly according to the above (2), wherein said projected part of said seal cap has an apex and a distal end side inclined portion which is extended from said apex toward a distal end of said seal cap part and becomes gradually lower in a projection height thereof toward said distal end of said seal cap; and said distal end side inclined portion is pressed against an outer surface of said annular head portion through said polyparaxylylene coating and kept in close contact with said outer surface thereof.

(4) A syringe assembly according to any one of the above (1) through (3), which is subjected to high-pressure steam sterilization or ethylene oxide gas sterilization.

(5) A syringe assembly according to any one of the above (1) through (4), wherein said outer cylinder is formed of cyclic polyolefin, and said seal cap is formed of thermoplastic elastomer.

The prefilled syringe is constructed as described below.

(6) A prefilled syringe comprising a syringe assembly according to any one of the above (1) through (5), a gasket which is accommodated inside said outer cylinder and liquid-tightly slidable inside said outer cylinder, and a medical agent filled inside a space formed of said outer cylinder and said gasket.

The seal cap of the present invention for the outer cylinder is constructed as described below.

(7) A seal cap, for an outer cylinder, mounting on said outer cylinder having an outer cylinder body part, a cylindrical piercing needle mounting part provided at a distal end portion of said outer cylinder body part and having an annular head portion and an annular concave portion formed at a proximal end of said annular head portion, and a piercing needle, having a piercing needle tip at a distal end thereof, whose proximal end portion is inserted into said piercing needle mounting part and fixed thereto, wherein said seal cap has a closed distal end part, an open proximal end part, a piercing needle mounting part-accommodating part positioned at a side distal from said open proximal end part and accommodating said piercing needle mounting part, a hollow part continuous with a distal end of said piercing needle mounting part-accommodating part and having a piercing needle accommodating part accommodating said piercing needle, a pierceable part into which said piercing needle tip of said piercing needle accommodated inside said piercing needle accommodating part is pierceable, and a projected part formed on an inner surface of said piercing needle mounting part-accommodating part; a polyparaxylylene coating is formed on said inner surface of said piercing needle mounting part-accommodating part, when said seal cap is mounted on said outer cylinder, said piercing needle tip is pierced into said pierceable part of said seal cap; and when said projected part and said annular concave portion engage each other, said inner surface of said piercing needle mounting part-accommodating part and an outer surface of said piercing needle mounting part closely contact each other through said polyparaxylylene coating.

The above-described embodiments may be constructed as described below.

(8) A seal cap for an outer cylinder according to the above (7), wherein said projected part has an apex and a distal side inclined portion which is extended from said apex toward a distal end of said seal cap and becomes gradually lower in a projection height thereof toward said distal end of said seal cap; and when said seal cap is mounted on said outer cylinder, said distal end side inclined portion is pressed against an outer surface of said annular head portion through said polyparaxylylene coating and kept in close contact with said outer surface thereof.

(9) A seal cap for an outer cylinder according to the above (7) of (8), which is formed of thermoplastic elastomer.

The packaging body of the present invention for the syringe assembly is constructed as described below.

(10) A syringe assembly packaging body accommodating a plurality of syringe assemblies according to any one of the above (1) through (5), said packaging body comprising a container body whose upper surface is open and which has shape retainability, an outer cylinder holding member capable of holding a plurality of said syringe assemblies, a plurality of said syringe assemblies held by said outer cylinder holding member, a sheet-shaped lid member which airtightly seals said open upper surface of said container body and is peelable therefrom, and an air-permeable part, having bacteria impermeability and sterilizing gas permeability, which is provided on said container body or on said sheet-shaped lid member, and the packaging body has subjected to high-pressure steam sterilization or ethylene oxide gas sterilization.

The invention claimed is:

1. A syringe assembly comprising,
an outer cylinder having a cylindrical piercing needle mounting part, a piercing needle fixed said cylindrical piercing needle mounting part and a seal cap,
wherein said seal cap has a closed distal end part, an open proximal end part, a piercing needle mounting part-accommodating part accommodating a distal end portion of said piercing needle mounting part and a piercing needle accommodating part accommodating said piercing needle, and a pierceable part into which said piercing needle tip is pierceable,
a polyparaxylylene coating is provided on an inner surface of said piercing needle mounting part-accommodating part of said seal cap or/and on an outer surface of said piercing needle mounting part of said outer cylinder,
said seal cap is mounted on said outer cylinder;
said inner surface of said piercing needle mounting part-accommodating part of said seal cap and said outer surface of said piercing needle mounting part of said outer cylinder are kept in close contact with each other through said polyparaxylylene coating.

2. The syringe assembly according to claim 1, wherein said piercing needle mounting part of said outer cylinder has an annular head portion and an annular concave portion formed at a proximal end of said annular head portion; said piercing needle mounting part-accommodating part of said seal cap has a projected part formed on an inner surface thereof; and said annular concave portion of said piercing needle mounting part and said projected part formed on said inner surface of said piercing needle mounting part-accommodating part engage each other and closely contact each other through said polyparaxylylene coating.

3. The syringe assembly according to claim 2, wherein said projected part of said seal cap has an apex and a distal end side inclined portion which is extended from said apex toward a distal end of said seal cap part and becomes gradually lower in a projection height thereof toward said distal end of said seal cap; and said distal end side inclined portion is pressed against an outer surface of said annular head portion through said polyparaxylylene coating and kept in close contact with said outer surface thereof.

4. The syringe assembly according to claim 1, which is subjected to high-pressure steam sterilization or ethylene oxide gas sterilization.

5. The syringe assembly according to claim 1, wherein said outer cylinder is formed of cyclic polyolefin, and said seal cap is formed of thermoplastic elastomer.

6. A prefilled syringe comprising the syringe assembly according to claim 1, a gasket which is accommodated inside said outer cylinder and liquid-tightly slidable inside said outer cylinder, and a medical agent filled inside a space formed of said outer cylinder and said gasket.

7. A seal cap, for an outer cylinder, mounting on said outer cylinder having an outer cylinder body part, a cylindrical piercing needle mounting part provided at a distal end portion of said outer cylinder body part and having an annular head portion and an annular concave portion formed at a proximal end of said annular head portion, and a piercing needle fixed to said piercing needle mounting part,
wherein said seal cap has a closed distal end part, an open proximal end part, a piercing needle mounting part-accommodating part accommodating a distal end portion of said piercing needle mounting part and a piercing needle accommodating part accommodating said piercing needle, a pierceable part into which a piercing needle tip of said piercing needle is pierceable, and a projected part formed on an inner surface of said piercing needle mounting part-accommodating part;
a polyparaxylylene coating is formed on said inner surface of said piercing needle mounting part-accommodating part,
when said seal cap is mounted on said outer cylinder, said piercing needle tip is pierced into said pierceable part of said seal cap; and when said projected part and said annular concave portion engage each other, said inner surface of said piercing needle mounting part-accommodating part and an outer surface of said piercing needle mounting part closely contact each other through said polyparaxylylene coating.

8. The seal cap for an outer cylinder according to claim 7, wherein said projected part has an apex and a distal side inclined portion which is extended from said apex toward a distal end of said seal cap and becomes gradually lower in a projection height thereof toward said distal end of said seal cap; and when said seal cap is mounted on said outer cylinder, said distal end side inclined portion is pressed against an outer surface of said annular head portion through said polyparaxylylene coating and kept in close contact with said outer surface thereof.

9. The seal cap for an outer cylinder according to claim 7, which is formed of thermoplastic elastomer.

10. A syringe assembly packaging body accommodating a plurality of syringe assemblies according to claim 1,
wherein said packaging body comprises a container body whose upper surface is open and which has shape retainability, an outer cylinder holding member capable of holding a plurality of said syringe assemblies, a plurality of said syringe assemblies held by said outer cylinder holding member, a sheet-shaped lid member which airtightly seals said open upper surface of said container body and is peelable therefrom and an air-permeable part, having bacteria impermeability and sterilizing gas permeability, which is provided on said container body or on said sheet-shaped lid member, and said packaging body has subjected to high-pressure steam sterilization or ethylene oxide gas sterilization.

* * * * *